(12) United States Patent
Ciufolini et al.

(10) Patent No.: US 7,423,055 B2
(45) Date of Patent: *Sep. 9, 2008

(54) 2-(3-AMINOARYL)AMINO-4-ARYL-THIAZOLES FOR THE TREATMENT OF DISEASES

(75) Inventors: Marco Ciufolini, Lyons (FR); Camille Wermuth, Strasbourg (FR); Bruno Gielthen, Illkirch (FR); Alain Moussy, Paris (FR)

(73) Assignee: AB Science, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/632,101

(22) Filed: Aug. 1, 2003

(65) Prior Publication Data

US 2004/0110810 A1   Jun. 10, 2004

Related U.S. Application Data

(60) Provisional application No. 60/400,064, filed on Aug. 2, 2002.

(51) Int. Cl.
*A61K 31/44* (2006.01)
*C07D 417/04* (2006.01)
*C07D 417/14* (2006.01)

(52) U.S. Cl. .................. 514/342; 514/370; 546/270.4; 548/194; 544/364

(58) Field of Classification Search ............... 548/190, 548/194; 546/270.4; 514/342, 370
See application file for complete search history.

(56) References Cited

U.S. PATENT DOCUMENTS

| | | | |
|---|---|---|---|
| 3,192,225 A | | 6/1965 | Spivack et al. |
| 3,201,409 A | * | 8/1965 | Dexter et al. ................. 548/193 |
| 3,467,666 A | * | 9/1969 | Dexter et al. ................. 548/193 |
| 5,521,184 A | | 5/1996 | Zimmermann |
| 6,291,514 B1 | * | 9/2001 | Illig et al. .................... 514/447 |
| 2001/0044545 A1 | * | 11/2001 | Dhanoa et al. ............... 548/190 |
| 2003/0158199 A1 | * | 8/2003 | Stieber et al. ................ 514/242 |

FOREIGN PATENT DOCUMENTS

| WO | WO-96/01825 A1 * | 1/1996 |
|---|---|---|
| WO | WO 99/03854 A | 1/1999 |
| WO | WO 00/33842 A | 5/2000 |
| WO | WO 00/75120 A | 12/2000 |
| WO | WO 01/64200 A | 9/2001 |
| WO | WO 01/64674 A | 9/2001 |
| WO | WO 02/080925 A | 10/2002 |
| WO | WO 03/062215 A | 7/2003 |

OTHER PUBLICATIONS

Golub et al., Science, vol. 286, Oct. 15, 1999, pp. 531-537.*
Schantl et al., Synthetic Communications (1998), 28(8), pp. 1451-1462.*

* cited by examiner

*Primary Examiner*—Laura L. Stockton
(74) *Attorney, Agent, or Firm*—Foley & Lardner

(57) ABSTRACT

The present invention relates to novel compounds selected from 2-(3-aminoaryl)amino-4-aryl-thiazoles that selectively modulate, regulate, and/or inhibit signal transduction mediated by certain native and/or mutant tyrosine kinases implicated in a variety of human and animal diseases such as cell proliferative, metabolic, allergic, and degenerative disorders. More particularly, these compounds are potent and selective c-kit inhibitors.

30 Claims, 2 Drawing Sheets

2-(3-AMINOARYL)AMINO-4-ARYL-THIAZOLES FOR THE TREATMENT OF DISEASES

BACKGROUND OF THE INVENTION

The present invention relates to novel compounds selected from 2-(3-aminoaryl)amino-4-aryl-thiazoles that selectively modulate, regulate, and/or inhibit signal transduction mediated by certain native and/or mutant tyrosine kinases implicated in a variety of human and animal diseases such as cell proliferative, metabolic, allergic, and degenerative disorders. More particularly, these compounds are potent and selective c-kit inhibitors.

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation.

As of today, there are about 58 known receptor tyrosine kinases. Other tyrosine kinases are the well-known VEGF receptors (Kim et al., Nature 362, pp. 841-844, 1993), PDGF receptors, c-kit and the FLK family. These receptors can transmit signals to other tyrosine kinases including Src, Raf, Frk, Btk, Csk, Abl, Fes/Fps, Fak, Jak, Ack. etc.

Among tyrosine kinase receptors, c-kit is of special interest. Indeed, c-kit is a key receptor activating mast cells, which have proved to be directly or indirectly implicated in numerous pathologies for which the Applicant filed WO 03/004007, WO 03/004006, WO 03/003006, WO 03/003004, WO 03/002114, WO 03/002109, WO 03/002108, WO 03/002107, WO 03/002106, WO 03/002105, WO 03/039550, WO 03/035050, WO 03/035049, U.S. 60/359,652 and U.S. 60/359,651.

It was found that mast cells present in tissues of patients are implicated in or contribute to the genesis of diseases such as autoimmune diseases (rheumatoid arthritis, inflammatory bowel diseases (IBD)) allergic diseases, tumor angiogenesis, inflammatory diseases, and interstitial cystitis. In these diseases, it has been shown that mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-α, GM-CSF, MIP-1a, MIP-1b, MIP-2 and IFN-γ).

The c-kit receptor also can be constitutively activated by mutations leading to abnormal cell proliferation and development of diseases such as mastocytosis and various cancers.

For this reason, it has been proposed to target c-kit to deplete the mast cells responsible for these disorders.

The main objective underlying the present invention is therefore to find potent and selective compounds capable of inhibiting wild type and/or mutated c-kit.

Many different compounds have been described as tyrosine kinase inhibitors, for example, bis monocyclic, bicyclic or heterocyclic aryl compounds (WO 92/20642), vinylene-azaindole derivatives (WO 94/14808) and 1-cyclo-proppyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), selenoindoles and selenides (WO 94/03427), tricyclic polyhydroxylic compounds (WO 92/21660) and benzylphosphonic acid compounds (WO 91/15495), pyrimidine derivatives (U.S. Pat. No. 5,521,184 and WO 99/03854), indolinone derivatives and pyrrole-substituted indolinones (U.S. Pat. No. 5,792,783, EP 934 931, U.S. Pat. No. 5,834,504, U.S. Pat. No. 5,883,116, U.S. Pat. No. 5,883,113, U.S. Pat. No. 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343,940) and aryl and heteroaryl quinazoline (U.S. Pat. No. 5,721,237, U.S. Pat. No. 5,714,493, U.S. Pat. No. 5,710,158 and WO 95/15758).

However, none of these compounds have been described as potent and selective inhibitors of c-kit or of the c-kit pathway.

In connection with the present invention, we have found that compounds corresponding to the 2-(3-aminoaryl)amino-4-aryl-thiazoles are potent and selective inhibitors of c-kit or c-kit pathway. These compounds are good candidates for treating diseases such as autoimmunes diseases, inflammatory diseases, cancer and mastocytosis.

BRIEF SUMMARY OF THE INVENTION

Therefore, the present invention relates to compounds belonging to the 2-(3-amino)arylamino-4-aryl-thiazoles. These compounds are capable of selectively inhibiting signal transduction involving the tyrosine phosphokinase c-kit and mutant forms thereof. In a first embodiment, the invention is aimed at compounds of formula I, which may represent either free base forms of the substances or pharmaceutically acceptable salts thereof:

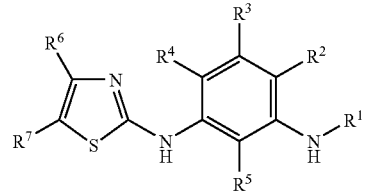

FORMULA I and wherein $R^1$ is:
a) a linear or branched alkyl group containing from 1 to 10 carbon atoms optionally substituted with at least one heteroatom, notably a halogen selected from I, Cl, Br and F, and/or bearing a pendant basic nitrogen functionality;
b) an aryl or heteroaryl group optionally substituted by an alkyl or aryl group optionally substituted with a heteroatom, notably a halogen selected from I, Cl, Br and F or bearing a pendant basic nitrogen functionality;
c) a —CO—NH—R, —CO—R, —CO—OR or a —CO—NRR' group, wherein R and R' are independently chosen from H or an aryl, heteroaryl, alkyl and cycloalkyl group optionally substituted with at least one heteroatom, notably a halogen selected from I, Cl, Br and F, and/or bearing a pendant basic nitrogen functionality;

$R^2$ is hydrogen, halogen or a linear or branched alkyl group containing from 1 to 10 carbon atoms, trifluoromethyl or alkoxy;

$R^3$ is hydrogen, halogen or a linear or branched alkyl group containing from 1 to 10 carbon atoms, trifluoromethyl or alkoxy;

$R^4$ is hydrogen, halogen or a linear or branched alkyl group containing from 1 to 10 carbon atoms, trifluoromethyl or alkoxy;

$R^5$ is hydrogen, halogen or a linear or branched alkyl group containing from 1 to 10 carbon atoms, trifluoromethyl or alkoxy;

$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy,
iv) H, a halogen selected from 1, F, Cl or Br; NH2, NO2 or SO2—R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality; and $R^7$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from 1, F, Cl or Br; NH2, NO2 or SO2—R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality;

DETAILED DESCRIPTION OF INVENTION

The present invention provides compounds belonging to the 2-3(-amino)arylamino-4-aryl-thiazoles, such as those described above with reference to Formula I. These compounds are capable of selectively inhibiting signal transduction involving the tyrosine phosphokinase c-kit and mutant forms thereof.

In another preferred embodiment, when $R^1$ has the meaning depicted in c) above, the invention is directed to compounds of the following formula:

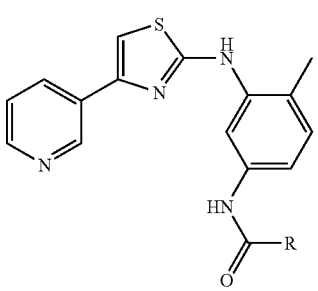

wherein R is H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted by an alkyl, a cycloalkyl, an aryl or heteroaryl group optionally substituted with a heteroatom, notably a halogen selected from I, Cl, Br and F and/or bearing a pendant basic nitrogen functionality.

Among the particular compounds in which R1 has the meaning as depicted in c) above, the invention is directed to amide-aniline compounds of the following formula:

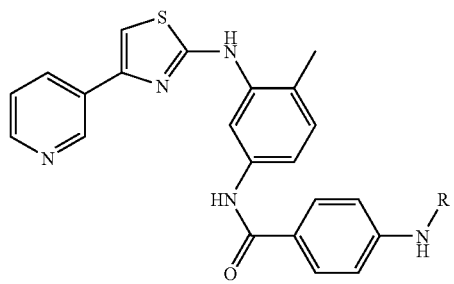

wherein R is H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted with a heteroatom, notably a halogen selected from I, Cl, Br and F and/or bearing a pendant basic nitrogen functionality; or a a cycloalkyl, an aryl or heteroaryl group optionally substituted with a cycloalkyl, an aryl or heteroaryl group optionally substituted with a heteroatom, notably a halogen selected from I, Cl, Br and F and/or bearing a pendant basic nitrogen functionality;
a —SO2—R group wherein R is an alkyl, cycloalkyl, aryl or heteroaryl optionally substituted with an heteroatom, notably a halogen selected from I, Cl, Br and F and/or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Among the particular compounds in which R1 has the meaning as depicted in c) above, the invention is directed to amide-benzylamine compounds of the following formula:

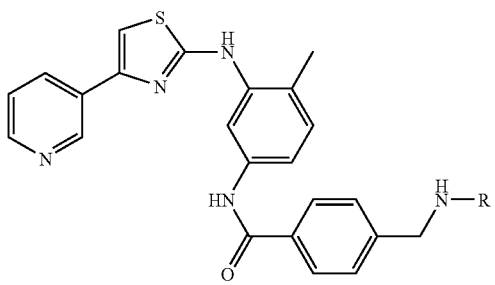

wherein R is H or an organic group that can be selected for example from a linear or branched alkyl group containing from 1 to 10 carbon atoms optionally substituted with at least one heteroatom, notably a halogen selected from I, Cl, Br and F, and/or bearing a pendant basic nitrogen functionality; a cycloalkyl, aryl or heteroaryl group optionally substituted with an heteroatom, notably a halogen selected from I, Cl, Br and F or bearing a pendant basic nitrogen functionality; or an alkyl, cycloalkyl, aryl or heteroaryl group substituted by a alkyl, cycloalkyl, aryl or heteroaryl group optionally substituted with a heteroatom, notably a halogen selected from I, Cl, Br and F or bearing a pendant basic nitrogen functionality;

a —SO2—R group wherein R is an alkyl, cycloalkyl, aryl or heteroaryl group optionally substituted with an heteroatom, notably a halogen selected from I, Cl, Br and F or bearing a pendant basic nitrogen functionality; or a —CO—R or a —CO—NRR' group, wherein R and R' are independently chosen from H or an aryl heteroaryl, alkyl and cycloalkyl group optionally substituted with at least one heteroatom and/or bearing a pendant basic nitrogen functionality.

Among the particular compounds in which R1 has the meaning as depicted in c) above, the invention is directed to amide-phenol compounds of the following formula:

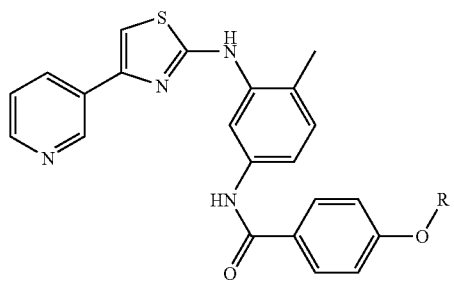

wherein R is H or an organic group that can be selected for example from a linear or branched alkyl group containing from 1 to 10 carbon atoms optionally substituted with at least one heteroatom, notably a halogen selected from I, Cl, Br and F, and/or bearing a pendant basic nitrogen functionality;

a cycloalkyl, aryl or heteroaryl group optionally substituted with a heteroatom, notably a halogen selected from I, Cl, Br and F and/or bearing a pendant basic nitrogen functionality; or an alkyl, cycloalkyl, aryl or heteroaryl group substituted by a alkyl, cycloalkyl, aryl or heteroaryl group optionally substituted with a heteroatom, notably a halogen selected from I, Cl, Br and F and/or bearing a pendant basic nitrogen functionality;

a —SO2—R group wherein R is an alkyl, cycloalkyl, aryl or heteroaryl group optionally substituted with an heteroatom, notably a halogen selected from I, Cl, Br and F and/or bearing a pendant basic nitrogen functionality; or a —CO—R or a —CO—NRR' group, wherein R and R' are independently chosen from H or an aryl, heteroaryl, alkyl and cycloalkyl group optionally substituted with at least one heteroatom and/or bearing a pendant basic nitrogen functionality.

Among the particular compounds in which R1 has the meaning as depicted in c) above, the invention is directed to urea compounds of the following formula:

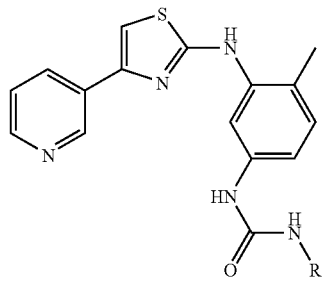

wherein R is H or an organic group that can be selected for example from a linear or branched alkyl group containing from 1 to 10 carbon atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality.

Among the particular compounds in which R1 has the meaning as depicted in a) and b) above, the invention is directed to N-Aminoalkyl-N'-thiazol-2-yl-benzene-1,3-diamine compounds of the following formula:

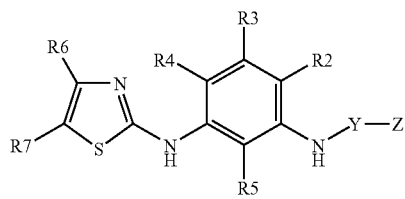

wherein Y is a linear or branched alkyl group containing from 1 to 10 carbon atoms;

wherein Z represents an aryl or heteroaryl group, optionally substituted at one or more ring position with any permutation of the following groups:

a halogen such as F, Cl, Br, I;

a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an O—R, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NRaRb, where Ra and Rb represents a hydrogen, or a linear or branched alkyl group containing from 1 to 10 carbon atoms atoms optionally substituted with at least one heteroatom (for example a halogen) and/or bearing a pendant basic nitrogen functionality or a cycle; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a COOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a CONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCOOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $OSO_2R$, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an beteroatom, notably a halogen selected from I, Cl, Br and F, and/or bearing a pendant basic nitrogen functionality;

an $NRaOSO_2Rb$, where Ra and Rb are a linear or branched alkyl group containing from 1 to 10 carbon atoms atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

$R^2$ is hydrogen, halogen or a linear or branched alkyl group containing from 1 to 10 carbon atoms, trifluoromethyl or alkoxy;

$R^3$ is hydrogen, halogen or a linear or branched alkyl group containing from 1 to 10 carbon atoms, trifluoromethyl or alkoxy;

$R^4$ is hydrogen, halogen or a linear or branched alkyl group containing from 1 to 10 carbon atoms, trifluoromethyl or alkoxy;

$R^5$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

iv) H, a halogen selected from 1, F, Cl or Br; NH2, NO2 or SO2—R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality; and $R^7$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

iv) H, an halogen selected from I, F, Cl or Br; NH2, NO2 or SO2-R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality.

An example of preferred compounds of the above formula is depicted below:

001: 4-{[4-Methyl-3-(4-pyridin-3-yl-thiazol-2-ylamino)-phenylamino]-methyl}-benzoic acid methyl ester

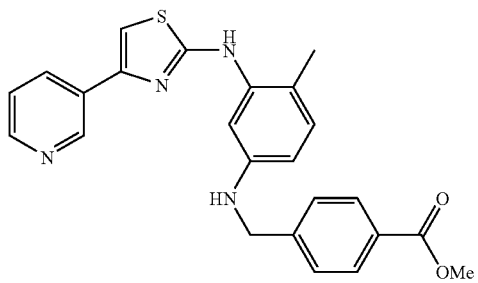

Among the compounds of formula I, the invention is particularly embodied by the compounds of the following formula II:

FORMULA II

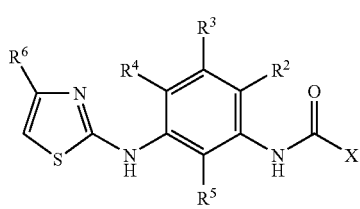

wherein X is R or NRR' and wherein R and R' are independently chosen from H, an aryl, a heteroaryl, an alkyl, or a cycloalkyl group optionally substituted with at least one heteroatom, such as for example a halogen chosen from F, I, Cl and Br and optionally bearing a pendant basic nitrogen functionality; or an aryl, a heteroaryl, an alkyl or a cycloalkyl group substituted with an aryl, a heteroaryl, an alkyl or a cycloalkyl group optionally substituted with at least one heteroatom, such as for example a halogen chosen from F, I, Cl and Br and optionally bearing a pendant basic nitrogen functionality, $R^2$ is hydrogen, halogen or a linear or branched alkyl group containing from 1 to 10 carbon atoms, trifluoromethyl or alkoxy;

$R^3$ is hydrogen, halogen or a linear or branched alkyl group containing from 1 to 10 carbon atoms, trifluoromethyl or alkoxy;

$R^4$ is hydrogen, halogen or a linear or branched alkyl group containing from 1 to 10 carbon atoms, trifluoromethyl or alkoxy;

$R^5$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

iv) H, a halogen selected from I, F, Cl or Br; NH2, NO2 or SO2—R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality.

In another alternative, substituent $R^6$, which in the formula II is connected to position 4 of the thiazole ring, may instead occupy position 5 of the thiazole ring.

Among the preferred compounds corresponding formula II, the invention is directed to compounds in which X is a substituted alkyl, aryl or heteroaryl group bearing a pendant basic nitrogen functionality represented for example by the structures a to f shown below, wherein the wavy line corresponds to the point of attachment to core structure of formula II:

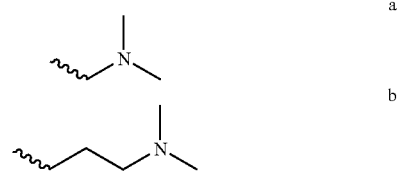

-continued

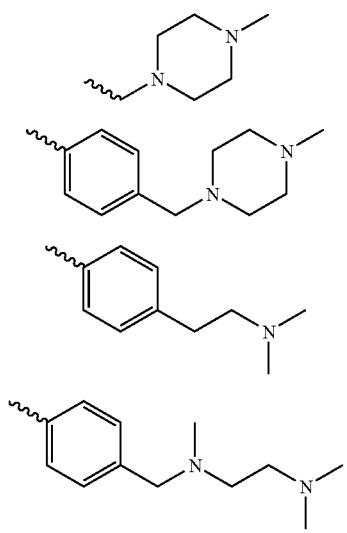

Among group a to f, X (see formula II) is preferentially group d.

Furthermore, among the preferred compounds of formula I or II, the invention concerns the compounds in which $R^2$ and $R^3$ are hydrogen. Preferentially, $R^4$ is a methyl group and $R^5$ is H. In addition, $R^6$ is preferentially a 3-pyridyl group (cf. structure g below), or a 4-pyridyl group (cf. structure h below). The wavy line in structure g and h correspond to the point of attachment to the core structure of formula I or II.

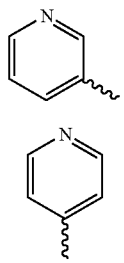

Thus, the invention contemplates:

1—A compound of formula II as depicted above, wherein X is group d and $R^6$ is a 3-pyridyl group.
2—A compound of formula II as depicted above, wherein X is group d and $R^4$ is a methyl group.
3—A compound of formula I or II as depicted above, wherein $R^1$ is group d and $R^2$ is H.
4—A compound of formula I or II as depicted above, wherein $R^1$ is group d and $R^3$ is H.
5—A compound of formula I or II as depicted above, wherein $R^1$ is group d and $R^2$ and/or $R^3$ and/or $R^5$ is H.
6—A compound of formula I or II as depicted above, wherein $R^6$ is a 3-pyridyl group and $R^3$ is a methyl group.
7—A compound of formula I or II as depicted above, wherein $R^6$ is a 3-pyridyl group and $R^2$ is H.
8—A compound of formula I or II as depicted above, wherein $R^2$ and/or $R^3$ and/or $R^5$ is H and $R^4$ is a methyl group.
9—A compound of formula I or II as depicted above wherein $R^2$ and/or $R^3$ and/or $R^5$ is H, $R^4$ is a methyl group and $R^6$ is a 3-pyridyl group.

Among the compounds of formula II, the invention is particularly embodied by the compounds wherein R2, R3, R5 are hydrogen, corresponding to the following formula II-1:

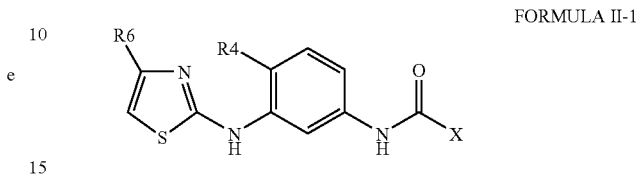

FORMULA II-1 wherein X is R or NRR' and wherein R and R' are independently chosen from H or an organic group that can be selected for example from a linear or branched alkyl group containing from 1 to 10 carbon atoms optionally substituted with at least one heteroatom or bearing a pendant basic nitrogen functionality; a cycloalkyl, an aryl or heteroaryl group optionally substituted with an heteroatom, notably a halogen selected from I, Cl, Br and F or bearing a pendant basic nitrogen functionality; or a a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a —SO2-R group wherein R is an alkyl, cycloalkyl, aryl or heteroaryl optionally substituted with a heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

$R^4$ is hydrogen, halogen or a linear or branched alkyl group containing from 1 to 10 carbon atoms, trifluoromethyl or alkoxy;

$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality.

In another alternative, substituent R6, which in the formula II is connected to position 4 of the thiazole ring, may instead occupy position 5 of the thiazole ring.

EXAMPLES

002: 4-(4-methyl-piperazni-1-ylmethyl)-N-[4-methyl-3-(4-pyridin-3-yl-thiazo-2-ylamino)-phenyl]-benzainide

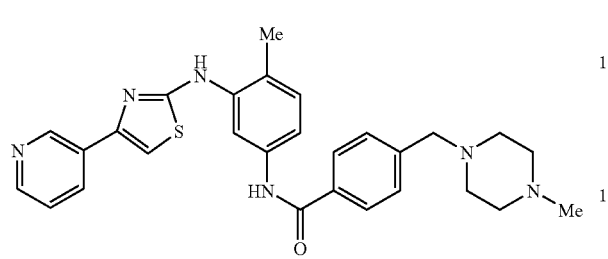

003: 4-(4-Methyl-piperazin-1-ylmethyl)-N-[3-(4-pyridin-3-yl-thiazol-2-ylamino)-phenyl]-benzamide

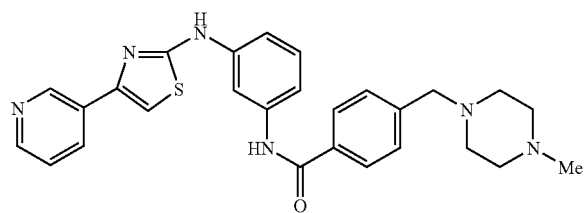

004: N-[4-Methyl-3-(4-phenyl-thiazol-2-ylamino)-phenyl]-4-(4-methyl-piperazin-1-ylmethyl)-benzamide

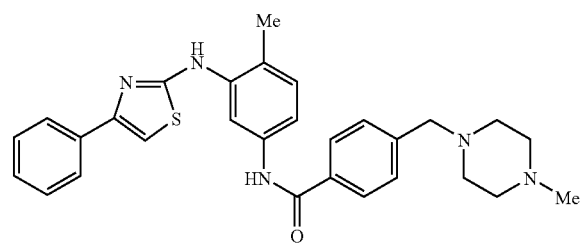

005: N-[3-([2,4']Bithiazolyl-2'-ylamino)-4-methyl-phenyl]-4-(4-methyl-piperazin-1-ylmethyl)-benzamide

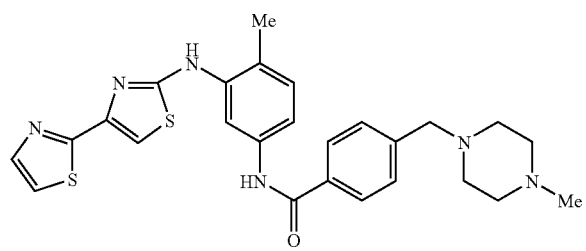

006: 4-(4-Methyl-piperazin-1-ylmethyl)-N-[4-methyl-3-(4-pyrazin-2-yl-thiazol-2-ylamino)-phenyl]-benzamide

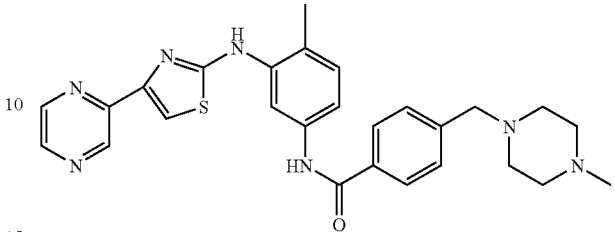

007: 2-[5-(3-Iodo-benzoylamino)-2-methyl-phenylamino]-thiazole-4-carboxylic acid ethyl ester

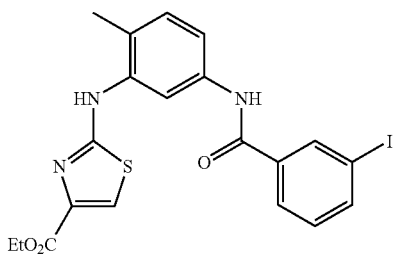

008: 2-{2-Methyl-5-[4-(4-methyl-piperazin-1-ylmethyl)-benzoylamino]-phenylamino}-thiazole-4-carboxylic acid ethyl ester

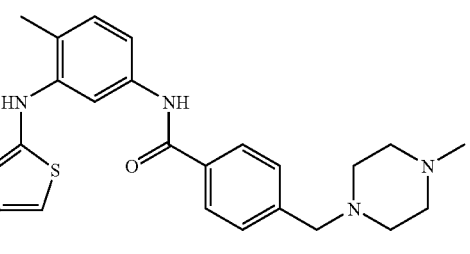

027: N-(4-chloro-3-(4-pyridin-3-yl-thiazol-2-ylamino)-phenyl)-4-(4-methyl-piperazin-1-ylmethyl)benzamide

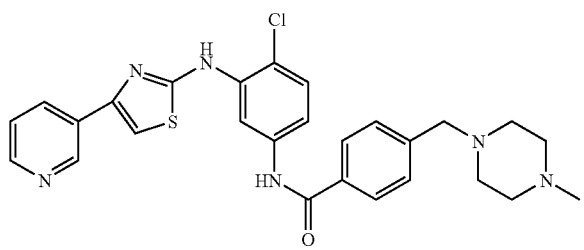

128: 3-Bromo-N-{3-[4-(4-chloro-phenyl)-5-methyl-thiazol-2-ylamino]-4-methyl-phenyl}-benzamide

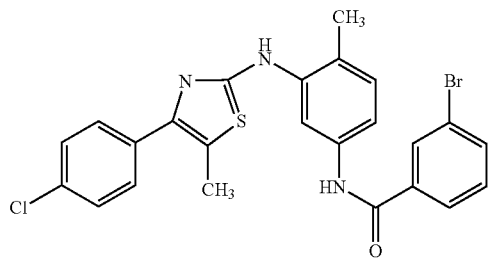

110: N-{3-[4-(4-Methoxy-phenyl)-thiazol-2-ylamino]-4-methyl-phenyl}-4-(4-methyl-piperazin-1ylmethyl)-benzamide

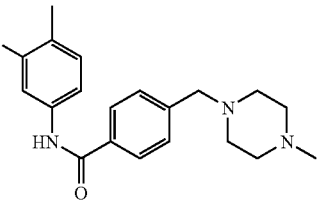

129: {3-[4-(4-Chloro-phenyl)-5-methyl-thiazol-2-ylamino]-4-methyl-phenyl}-carbamic acid isobutyl ester

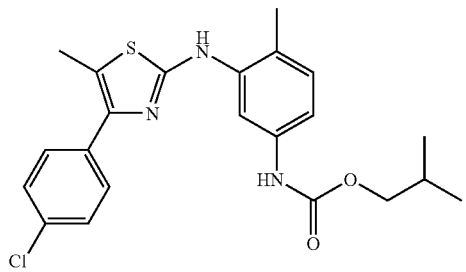

116: 4-(4-Methyl-piperazin-1-ylmethyl)-N-{4-methyl-3-[4-(3-trifluoromethyl-phenyl)-thiazol-2-ylamino]-phenyl}-benzamide 130: 2-[5-(3-Bromo-benzoylamino)-2-methyl-phenylamino]-5-(4-chloro-phenyl)-thiazole-4-carboxylic acid ethyl ester

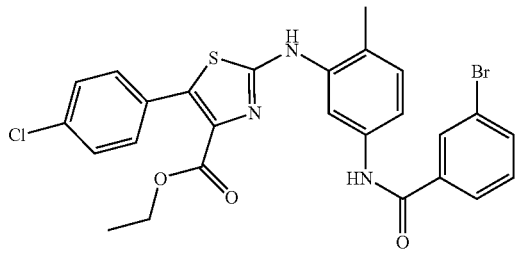

117: N-{4-Methyl-3-[4-(3-nitro-phenyl)-thiazol-2-ylamino]-phenyl}-4-(4-methyl-piperazin-1-ylmethyl)-benzamide 131: 2-[5-(3-Bromo-benzoylamino)-2-methyl-phenylamino]-5-(4-chloro-phenyl)-thiazole-4-carboxylic acid (2-dimethylamino-ethyl)-amide

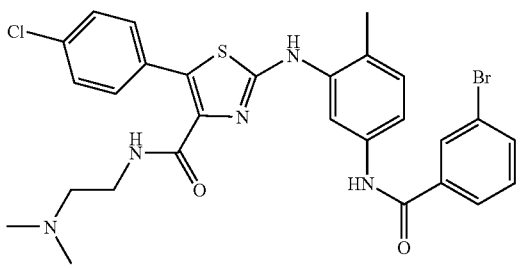

124: N-{3-[4-(2,5-Dimethyl-phenyl)-thiazol-2-ylamino]-4-methyl-phenyl}-4-(4-methyl-piperazin-1-ylmethyl)-benzamide

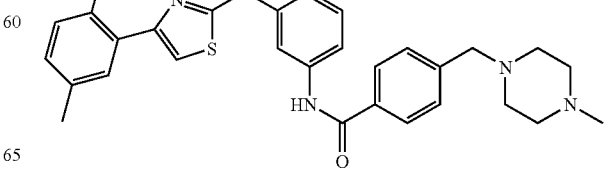

108: N-{3-[4-(4-Chloro-phenyl)-thiazol-2-ylamino]-4-methyl-phenyl}-4-(4-methyl-piperazin-1-ylmethyl)-benzamide

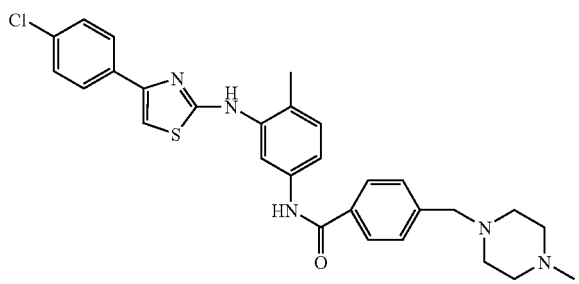

113: N-{3-[4-(3-Methoxy-phenyl)-thiazol-2-ylamino]-4-methyl-phenyl}-4-(4-methyl-piperazin-1-ylmethyl)-benzamide

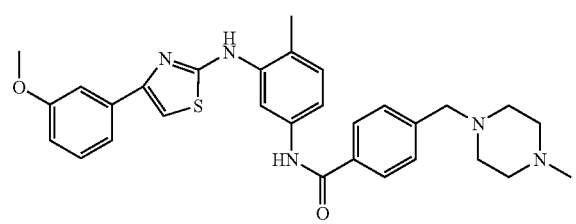

063: N-[4-Methyl-3-(4-pyridin-3-yl-thiazol-2-ylamino)-phenyl]-isonicotinamide

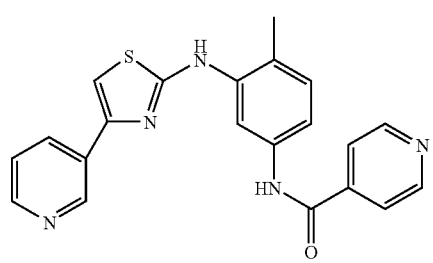

064: 2,6-Dichloro-N-[4-methyl-3-(4-pyridin-3-yl-thiazol-2-ylamino)-phenyl]-isonicotinamide

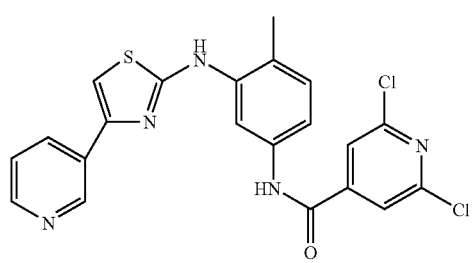

091: 3-Phenyl-propynoic acid [4-methyl-3-(4-pyridin-3-yl-thiazol-2-ylamino)-phenyl]-amide

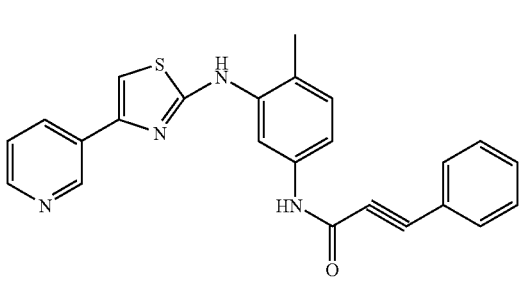

092: Cyclohexanecarboxylic acid [4-methyl-3-(4-pyridin-3-yl-thiazol-2-ylamino)-phenyl]-amide

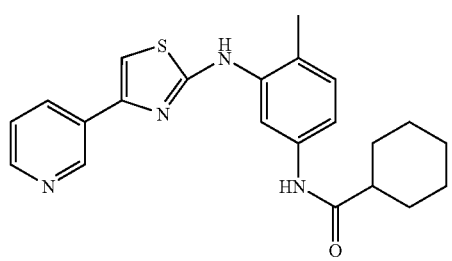

093: 5-[4-Methyl-3-(4-pyridin-3-yl-thiazol-2-ylamino)-phenylcarbamoyl]-pentanoic acid ethyl ester

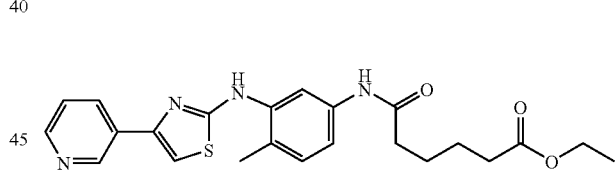

094: 1-Methyl-cyclohexanecarboxylic acid [4-methyl-3-(4-pyridin-3-yl-thiazol-2-ylamino)-phenyl]-amide

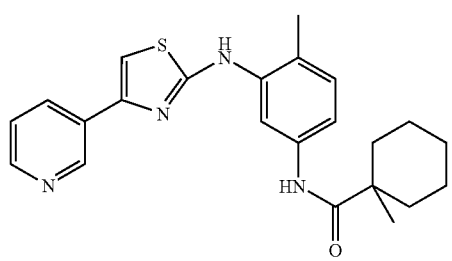

095: 4-tert-Butyl-cyclohexanecarboxylic acid [4-methyl-3-(4-pyridin-3-yl-thiazol-2-ylamino)-phenyl]-amide

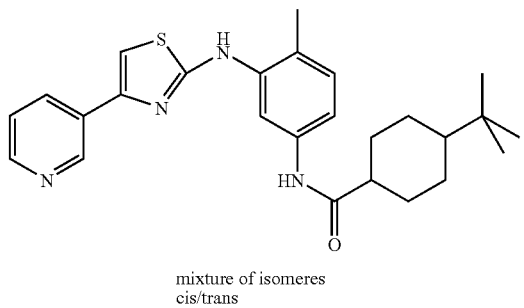

mixture of isomeres cis/trans

096: N-[4-Methyl-3-(4-pyridin-3-yl-thiazol-2-ylamino)-phenyl]-4-morpholin-4-yl-butyramide

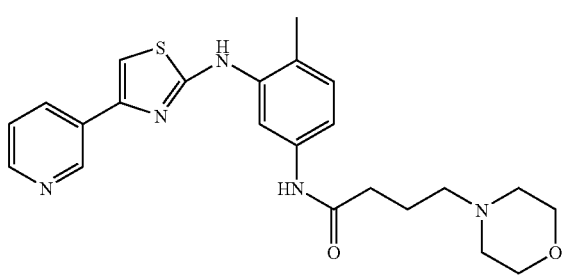

beige powder mp: 116-120° C. $^1$H RMN (DMSO-d$^6$) δ=1.80-2.00 (m, 2H); 2.29 (s, 3H); 2.30-2.45 (m, 6H); 3.55-3.65 (m, 6H); 7.15-7.25 (m, 2H); 7.46-7.50 (m, 2H); 7.52 (s, 1H); 8.35 (d, J=6.2 Hz, 1H); 8.55 (dd, J=1.5 Hz, J=4.7 Hz, 2H); 9.22 (s, 1H); 9.45 (s, 1H); 9.93 (s, 1H)

Among the compounds of formula II, the invention is particularly embodied by the compounds wherein X is a urea group, a —CO—NRR' group, corresponding to the [3-(thiazol-2-ylamino)-phenyl]-urea family and the following formula II-2:

FORMULA II-2

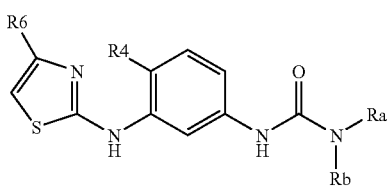

wherein Ra, Rb are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with a heteroatom, notably a halogen selected from I, Cl, Br and F or bearing a pendant basic nitrogen functionality;

a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, or bearing a pendant basic nitrogen functionality.

R$^4$ is hydrogen, halogen or a linear or branched alkyl group containing from 1 to 10 carbon atoms, trifluoromethyl or alkoxy;

R$^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.
iv) H, a halogen selected from I, F, Cl or Br; NH2, NO2 or SO2-R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality.

EXAMPLES

009: 1-(4-Methoxy-phenyl)-3-[4-methyl-3-(4-pyridin-3-yl-thiazol-2-ylamino)-phenyl]-urea

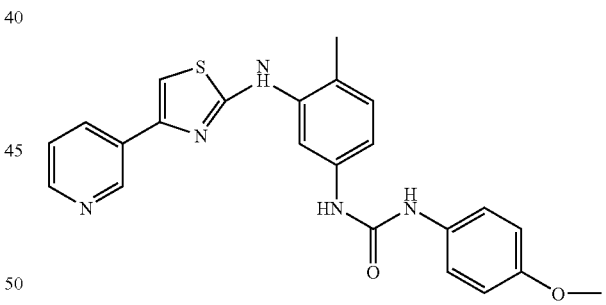

010: 1-(4-Bromo-phenyl)-3-[4-methyl-3-(4-pyridin-3-yl-thiazol-2-ylamino)-phenyl]-urea

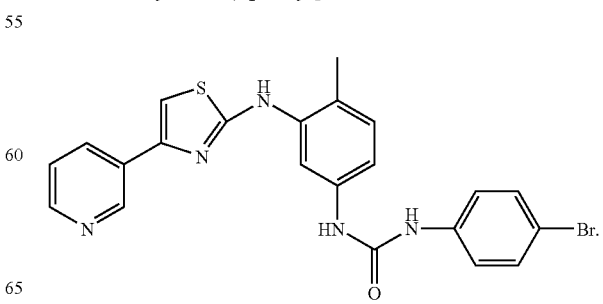

011: 1-[4-Methyl-3-(4-pyridin-3-yl-thiazol-2-ylamino)-phenyl]-3-(4-trifluoromethyl-phenyl)-urea

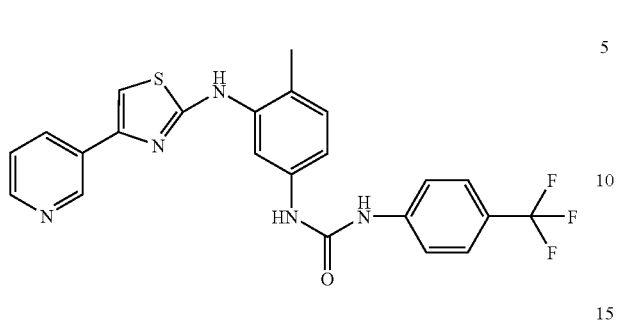

012: 1-(4-Fluoro-phenyl)-3-[4-methyl-3-(4-pyridin-3-yl-thiazol-2-ylamino)-phenyl]-urea

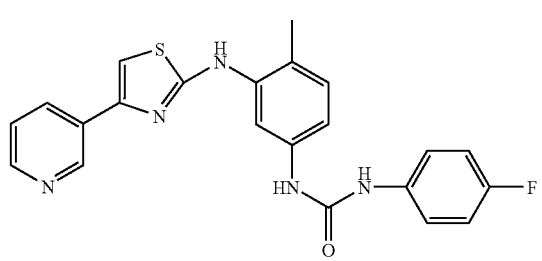

013: 1-[4-Methyl-3-(4-pyridin-3-yl-thiazol-2-ylamino)-phenyl]-3-(3,4,5-trimethoxy-phenyl)-urea

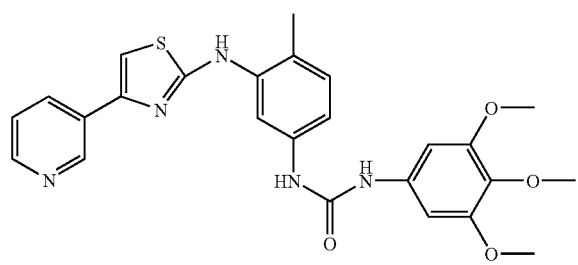

014: 4-{3-[4-Methyl-3-(4-pyridin-3-yl-thiazol-2-ylamino)-phenyl]-ureido}-benzoic acid ethyl ester

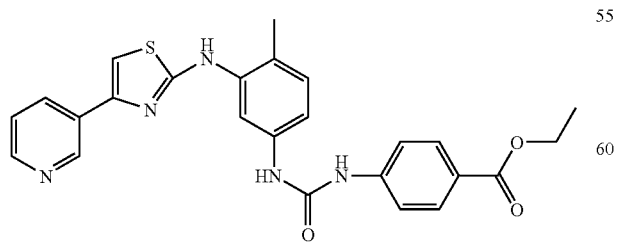

015: 1-[4-Methyl-3-(4-pyridin-3-yl-thiazol-2-ylamino)-phenyl]-3-thiophen-2-yl-urea

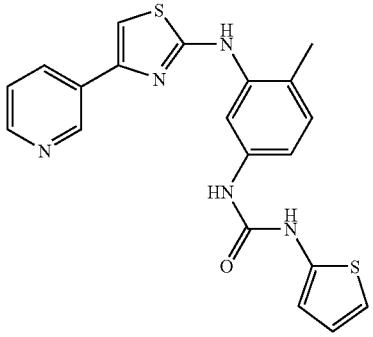

016: 1-Cyclohexyl-1-(N-Cyclohexy-formamide)-3-[4-methy-3-(4-pyridin-3-yl-thiazol-2-ylamino)-phenyl]-urea

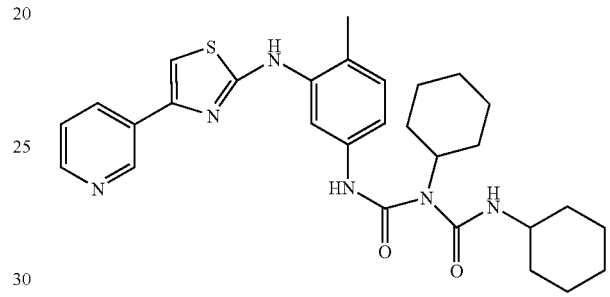

017: 1-(2,4-Dimethoxy-phenyl)-3-[4-methyl-2-(4-pryidin-3-yl-thiazol-2-ylamino)-phenyl]-urea

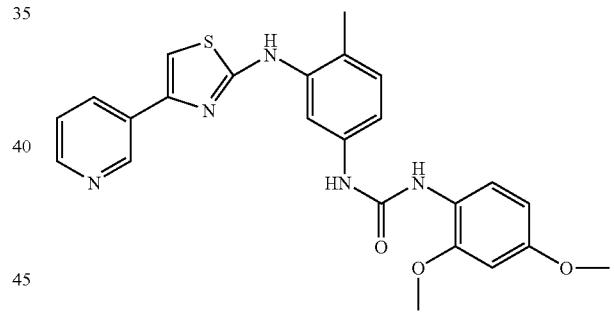

018: 1-(2-Iodo-phenyl)-1-(N-(2-Iodo-phenyl)-formamide)-3-[4-methyl-3-(4-pyridin-3-yl-thiazol-2-ylamino)-phenyl]-urea

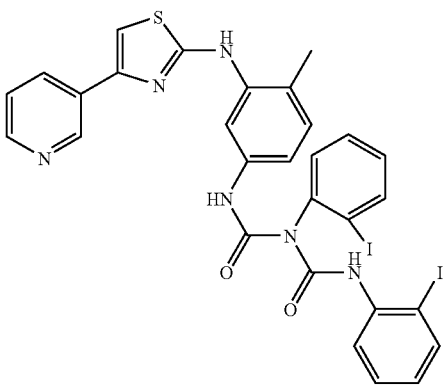

019: 1-(3,5-Dimethyl-isoxazol-4-yl)-3-[4-methyl-3-(4-pyridin-3-yl-thiazol-2-ylamino)-phenyl]-urea

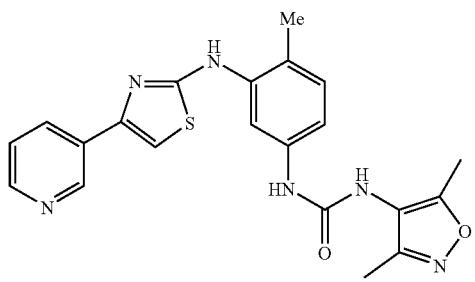

020: 1-(2-Iodo-phenyl)-3-[4-methyl-3-(4-pyridin-3-yl-thiazol-2-ylamino)-phenyl]-urea

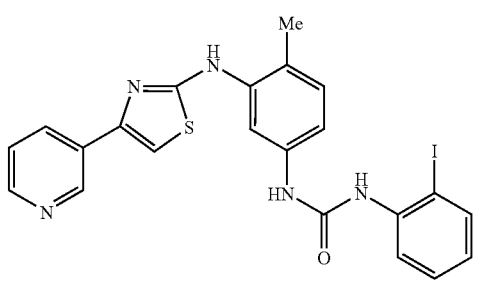

021: 1-(4-Difluoromethoxy-phenyl)-3-[4-methyl-3-(4-pyridin-3-yl-thiazol-2-ylamino)-phenyl]-urea

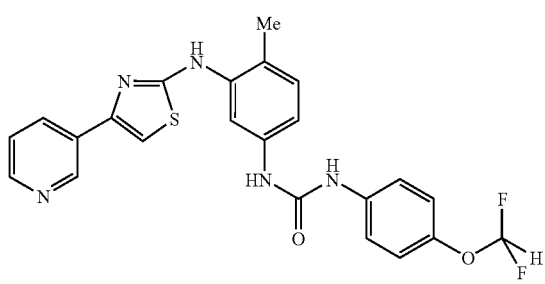

022: 1-(4-Dimethylamino-phenyl)-3-[4-methyl-3-(4-pyridin-3-yl-thiazol-2-ylamino)-phenyl]-urea

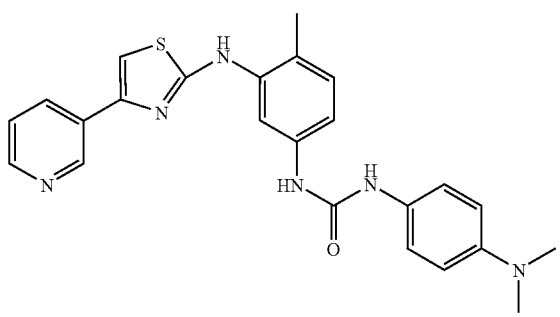

023: 1-(2-Fluoro-phenyl)-3-[4-methyl-3-(4-pyridin-3-yl-thiazol-2-ylamino)-phenyl]-urea

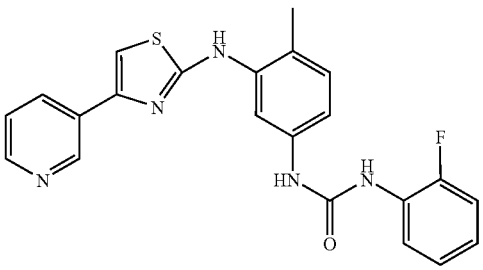

light brown powder mp: 203-206° C. $^1$H NMR (DMSO-d$^6$): δ=2.24 (s, 3H); 6.98-7.00 (m, 2H); 7.10-7.23 (m, 3H); 7.40 (m, 1H); 7.48 (s, 1H); 8.25 (m, 1H); 8.37 (d, J=7.8 Hz, 1H); 8.51 (m, 3H); 9.03 (s, 1H); 9.19 (s, 1H); 9.39 (s, 1H)

024: 1-(2-Chloro-phenyl)-3-[4-methyl-3-(4-pyridin-3-yl-thiazol-2-ylamino)-phenyl]-urea

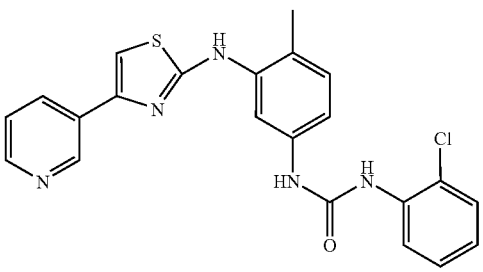

025: 1-(3-Fluoro-phenyl)-3-[4-methyl-3-(4-pyridin-3-yl-thiazol-2-ylamino)-phenyl]-urea

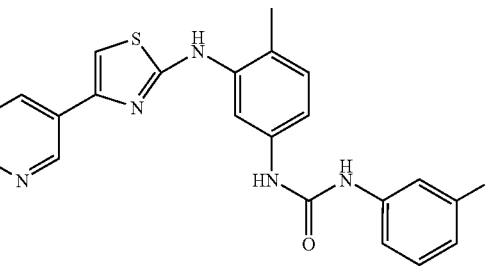

white powder mp: 210-215° C. $^1$H NMR (DMSO-d$^6$): δ 2.24 (s, 3H); 6.79 (t, J=6.3 Hz, 1H); 6.99 (m, 1H); 7.09-7.14 (m, 2H); 7.30 (m, 1H); 7.41 (t, J=4.7 Hz, 1H); 7.48 (s, 1H); 7.56 (d, J=1.2 Hz, 1H); 8.39 (d, J=8.0 Hz, 1H); 8.49-8.52 (m, 2H); 8.71 (s, 1H); 8.87 (s, 1H); 9.18 (s, 1H); 9.38 (s, 1H)

026: 1-[4-Methyl-3-(4-pyridin-3-yl-thiazol-2-ylamino)-phenyl]-3-p-tolyl-urea

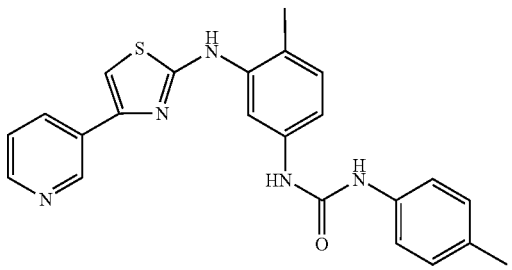

white powder mp: 238-240° C. $^1$H RMN (DMSO-d$^6$) δ=2.29 (s, 3H); 2.31 (s, 3H); 7.05 (d, J=6.2 Hz, 1H); 7.10-1.16 (m, 3H); 7.42-7.49 (m, 3H); 7.53 (s, 1H); 8.35-8.62 (m, 5H); 9.22 (d, J=1.6 Hz, 1H); 9.43 (s, 1H)

Among the compounds of formula II, the invention is particularly embodied by the compounds wherein X is a-substituted Aryl group, corresponding to the N-[3-(Thiazol-2-ylamino)-phenyl]-amide family and the following formula II-3:

FORMULA II-3

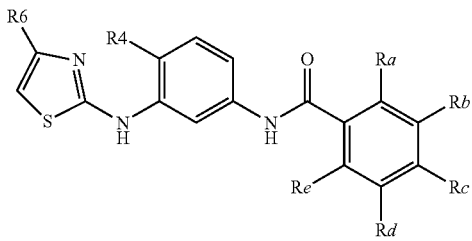

wherein Ra, Rb, Rc, Rd, Re are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a —SO2-R group wherein R is an alkyl, cycloalkyl, aryl or heteroaryl optionally substituted with a heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and or bearing a pendant basic nitrogen functionality;

Ra, Rb, Rc, Rd, Re may also be
a halogen such as I, Cl, Br and F
a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;

a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

a COOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a CONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an NHCOOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $OSO_2R$, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $NRaOSO_2Rb$, where Ra and Rb are a linear or branched alkyl group containing from 1 to 10 carbon atoms atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

a CN group a trifluoromethyl group $R^4$ is hydrogen, halogen or a linear or branched alkyl group containing from 1 to 10 carbon atoms, trifluoromethyl or alkoxy;

$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

iv) H, a halogen selected from 1, F, Cl or Br; NH2, NO2 or SO2-R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality.

EXAMPLES

028: 3-Bromo-N-[4-methyl-3-(4-pyridin-3-yl-thiazol-2-ylamino)-phenyl]-benzamide

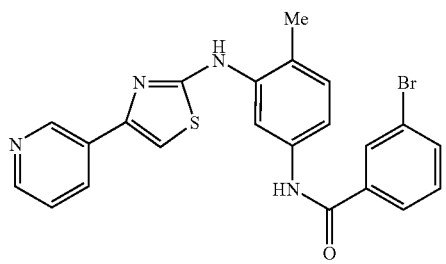

029: 3-Iodo-N-[4-methyl-3-(4-pyridin-3-yl-thiazol-2-ylamino)-phenyl]-benzamide

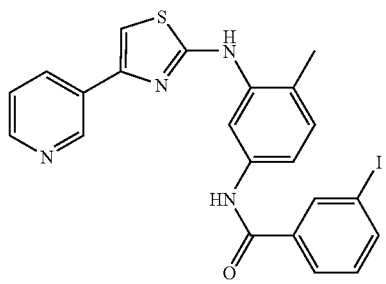

030: 4-Hydroxymethyl-N-[4-methyl-3-(4-pyridin-3-yl-thiazol-2-ylamino)-phenyl]-benzamide

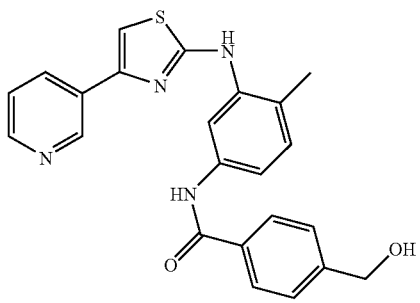

031: 4-Amino-N-[4-methyl-3-(4-pyridin-3-yl-thiazol-2-ylamino)-phenyl]-benzamide

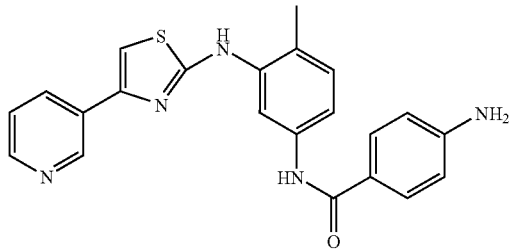

032: 2-Iodo-N-[4-methyl-3-(4-pyridin-3-yl-thiazol-2-ylamino)-phenyl]-benzamide

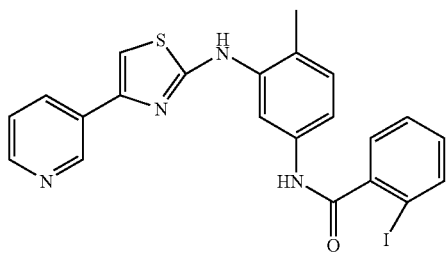

033: 4-Iodo-N-[4-methyl-3-(4-pyridin-3-yl-thiazol-2-ylamino)-phenyl]-benzamide

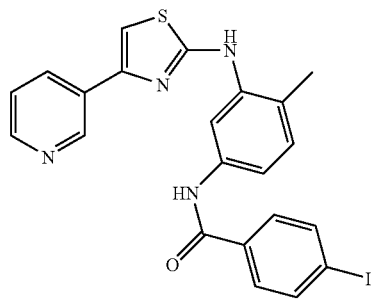

034: 4-(3-{4-[4-Methyl-3-(4-pyridin-3-yl-thiazol-2-ylamino)-phenylcarbamoyl]-phenyl}-ureido)-benzoic acid ethyl ester

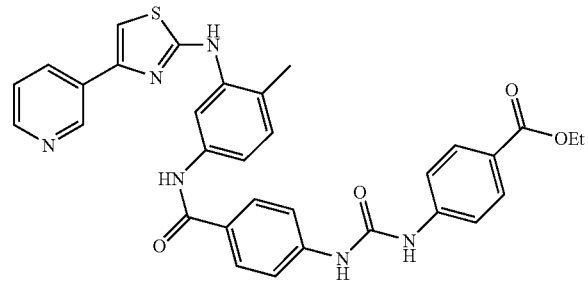

035: N-[4-Methyl-3-(4-pyridin-3-yl-thiazol-2-ylamino)-phenyl]-4-[3-(4-trifluoromethyl-phenyl)-ureido]-benzamide

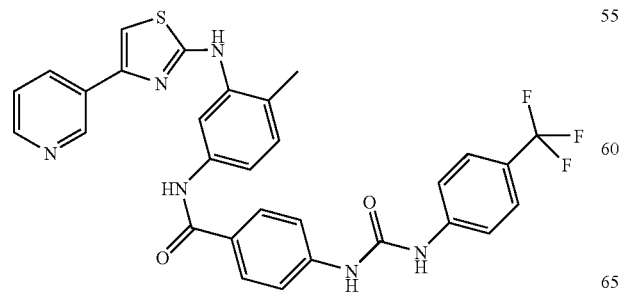

036: 4-[3-(4-Bromo-phenyl)-ureido]-N-[4-methyl-3-(4-pyridin-3-yl-thiazol-2-ylamino)-phenyl]-benzamide

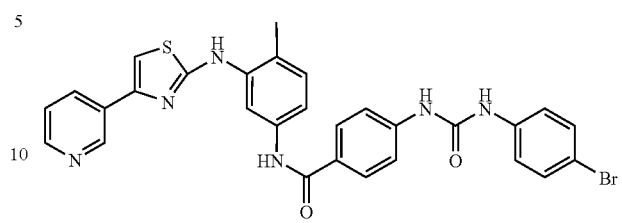

037: 4-Hydroxy-N-[4-mehtyl-3-(4-pyridin-3-yl-thiazol-2-ylamino)-phenyl]-benzamide

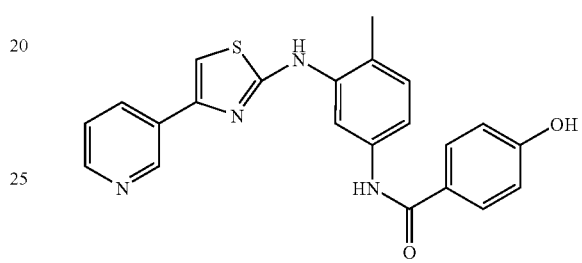

038: N-[4-Methyl-3-(4-pyridin-3-yl-thiazol-2-ylamino)-phenyl]-4-(3-thiophen-2-yl-ureido)-benzamide

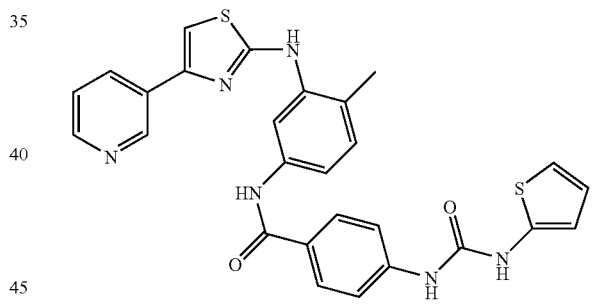

039: 4-[3-(3,5-Dimethyl-isoxazol-4-yl)-ureido]-N-[4-methyl-3-(4-pyridin-3-yl-thiazol-2-ylamino)-phenyl]-benzamide

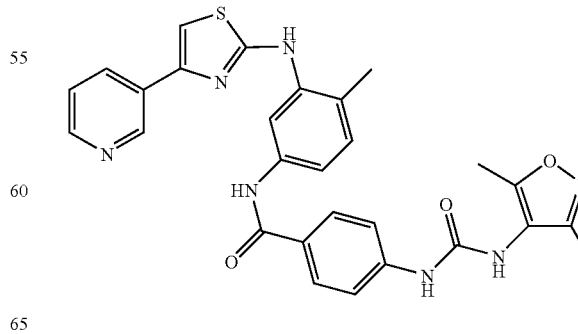

040: 4-[3-(4-Methoxy-phenyl)-ureido]-N-[4-methyl-3-(4-pyridin-3-yl-thiazol-2-ylamino)-phenyl]-benzamide

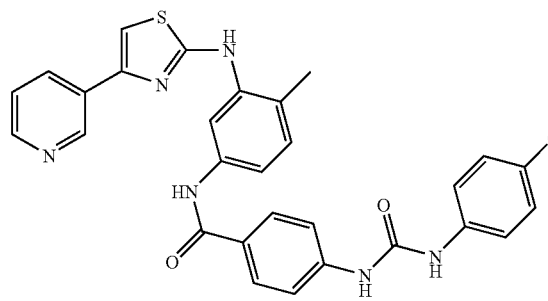

041: 4-[3-(4-Difluoromethoxy-phenyl)-ureido]-N-[4-methyl-3-(4-pyridin-3-yl-thiazol-2-ylamino)-phenyl]-benzamide

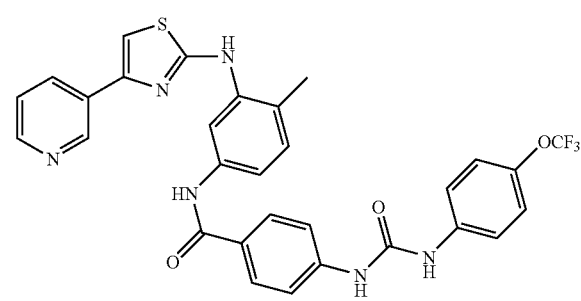

042: Thiophene-2-sulfonic acid 4-[4-methyl-3-(4-pyridin-3-yl-thiazol-2-ylamino)-phenylcarbamoyl]-phenyl ester

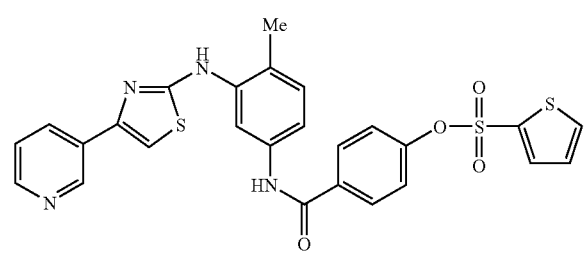

043: 4-Iodo-benzenesulfonic acid 4-[4-methyl-3-(4-pyridin-3-yl-thiazol-2-ylamino)-phenylcarbamoyl]-phenyl ester

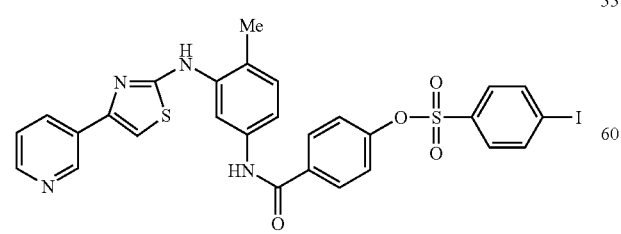

044: N-[4-Methyl-3-(4-pyridin-3-yl-thiazol-2-ylamino)-phenyl]4-(thiophene-2-sulfonylamino)-benzamide

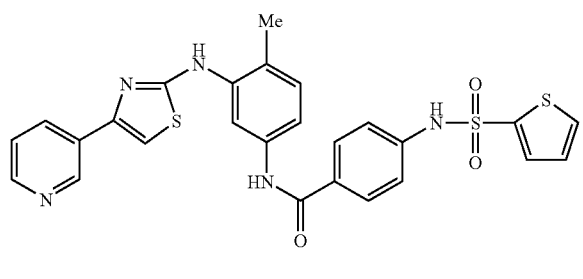

brown powder mp: 230-233° C. $^1$H NMR (DMSO-d$^6$) δ=2.29 (s, 3H); 7.15-7.18 (m, 2H); 7.22-7.32 (m, 3H); 7.48 (m, 2H); 7.67 (dd, J=1.3 Hz, J=3.7 Hz, 1H); 7.90-7.96 (m, 3H); 8.38-8.42 (m, 1H); 8.51 (m, 1H); 8.57 (d, J=1.9 Hz, 1H); 9.17 (d, J=1.7 Hz, 1H); 9.44 (s, 1H); 10.12 (s,1H); 10.82 (s, 1H)

045: 3-Fluoro-N-[4-methyl-3-(4-pyridin-3-yl-thiazol-2-ylamino)-phenyl]-benzamide

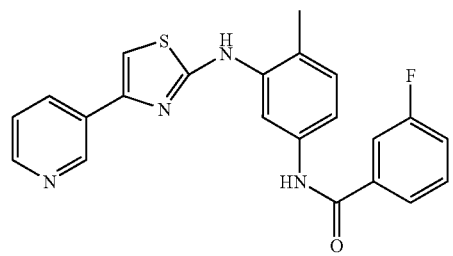

off-white foam mp: 184-186° C. $^1$H NMR (CD$_3$OD-d$^4$): δ=2.23 (s, 3H); 7.12-7.14 (m, 2H); 7.20-7.23 (m, 2H); 7.30 (m, 1H); 7.43 (m, 1H); 7.50 (m, 1H); 7.66 (d, J=1.0 Hz, 1H); 8.23 (m, 1H); 8.33 (m, 1H); 8.38 (s, 1H); 8.98 (s, 1H)

046: N-[4-Methyl-3-(4-pyridin-3-yl-thiazol-2-ylamino)-phenyl]-4-pyridin-4-yl-benzamide

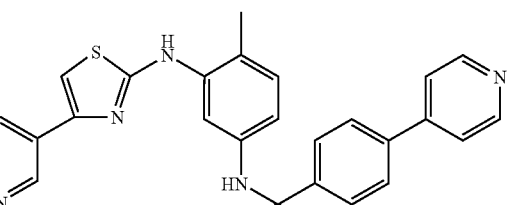

yellow powder mp: 254-256° C. $^1$H NMR (DMSO-d$^6$): δ 2.34 (s, 3H); 7.28 (d, J=8.0 Hz, 1H); 7.45-7.49 (m, 2H); 7.54 (s, 1H); 7.78 (t, J=7.6 Hz, 1H); 7.89-7.91 (m, 2H); 8.10 (t, J=7.8 Hz, 2H); 8.37-8.42 (m, 2H); 8.55 (d, J=4.7 Hz, 1H); 8.73-8.77 (m, 3H); 9.24 (s, 1H); 9.52 (s, 1H); 10.43 (s, 1H)

047: 4-Dimethylamino-N-[4-methyl-3-(4-pyridin-3-yl-thiazol-2-ylamino)-phenyl]-benzamide 050: 4-Isopropoxy-N-[4-methyl-3-(4-pyridin-3-yl-thiazol-2-ylamino)-phenyl]-benzamide

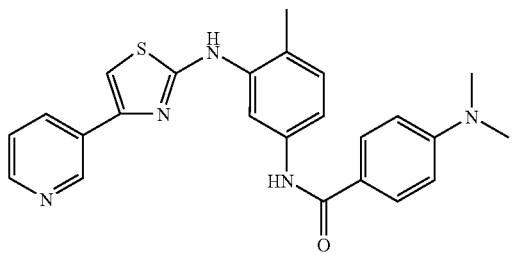

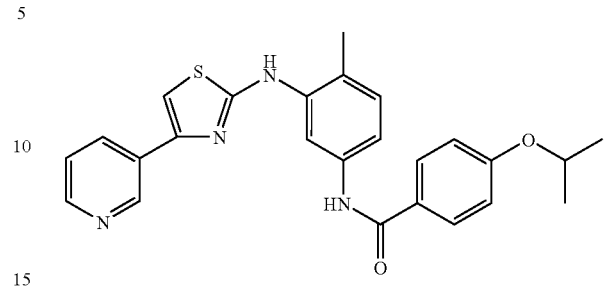

beige powder mp: 147-150° C. $^1$H NMR (DMSO-d$^6$): δ 2.25 (s, 3H); 2.99 (s, 6H); 6.76 (d, J=8.9 Hz, 2H); 7.16 (d, J=8.3 Hz, 1H); 7.35 (d, J=2.0 Hz, 1H); 7.44-7.47 (m, 2H); 7.86-7.89 (m, 2H); 8.34-8.36 (m, 1H); 8.48-8.50 (m, 1H); 8.56-8.57 (m, 1H); 9.16 (s, 1H); 9.44 (s, 1H); 9.85 (s, 1H)

048: 2-Fluoro-5-methyl-N-[4-methyl-3-(4-pyridin-3-yl-thiazol-2-ylamino)-phenyl]-benzamide brown powder mp: 154-155° C. $^1$H RMN (DMSO-d$^6$) δ=1.34 (d, J=5.9 Hz, 6H); 4.72 (hept, J=5.9 Hz, 1H); 7.01 (d, J=7.0 Hz, 2H); 7.18 (d, J=8.5 Hz, 1H); 7.35-7.44 (m, 2H); 7.46 (s, 1H); 7.94 (dd, J=2.0 Hz, J=6.7 Hz, 2H); 8.32 (d, J=8.3 Hz, 1H); 8.48 (dd, J=3.3 Hz, J=4.8 Hz, 1H); 8.58 (d, J=2.0 Hz, 1H); 9.15 (d, J=1.8 Hz, 1H); 9.43 (s, 1H); 10.4 (s, 1H)

051: Benzo[1,3]dioxole-5-carboxylic acid [4-methyl-3-(4-pyridin-3-yl-thiazol-2-ylamino)-phenyl]-amide

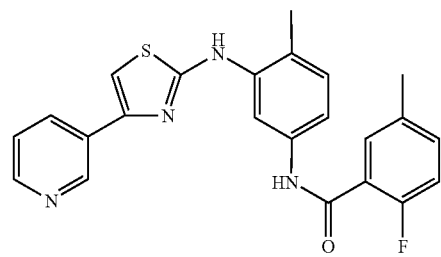

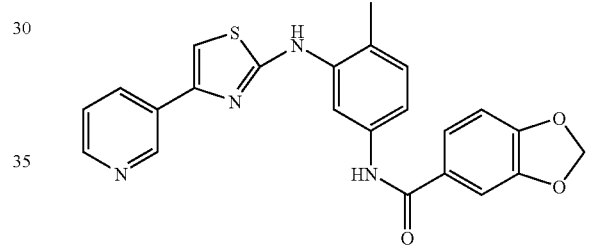

brown orange powder mp: 103-106° C. $^1$H RMN (DMSO-d$^6$) δ=2.26 (s, 3H); 2.35 (s, 3H); 7.17-7.47 (m, 7H); 8.29 (dd, J=1.6 Hz, J=7.9 Hz, 1H); 8.47 (d, J=3.5 Hz, 1H); 8.57 (s, 1H); 9.15 (d, J=2.0 Hz, 1H); 9.44 (s, 1H); 10.33 (s, 1H)

049: 4-tert-Butyl-N-[4-methyl-3-(4-pyridin-3-yl-thiazol-2-ylamino)-phenyl]-benzamide brown orange powder mp: 130-132° C. $^1$H RMN (DMSO-d$^6$) δ=2.23 (s, 3H); 6.10 (s, 2H); 7.03 (d, J=8.1 Hz, 1H); 7.15 (d, J=8.3 Hz, 1H); 7.25-7.55 (m, 6H); 8.26 (s, 1H); 8.45 (dd, J=1.5 Hz, J=4.7, 1H); 8.55 (d, J=2.0 Hz, 1H); 9.12 (d, J=1.7 Hz, 1H); 9.40 (s, 1H); 10.01 (s, 1H)

052: N-[4-Methyl-3-(4-pyridin-3-yl-thiazol-2-ylamino)-phenyl]-3-(2-morpholin-4-yl-ethoxy)-benzamide

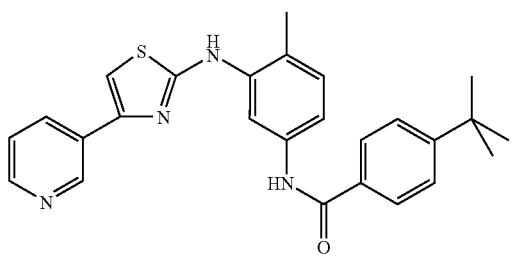

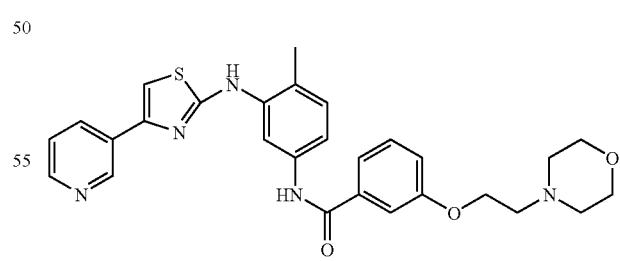

brown powder mp: 145-150° C. $^1$H RMN (DMSO-d$^6$) δ=1.32 (s, 9H); 2.04 (s, 3H); 7.18 (d, J=8.4 Hz, 1H); 7.35-7.44 (m, 2H); 7.46 (s, 1H); 7.55 (d, J=8.5 Hz, 1H); 7.90 (d, J=8.5 Hz, 1H); 8.32 (d, J=7.9 Hz, 1H); 8.47 (dd, J=1.5 Hz, J=4.7 Hz, 1H); 8.60 (d, J=2.0 Hz, 1H); 9.15 (d, J=1.7 Hz, 1H); 9.43 (s, 1H); 10.15 (s, 1H)

beige yellow powder mp: 75-80° C. $^1$H RMN (DMSO-d$^6$) δ=2.10-2.25 (m, 4H); 2.50-2.60 (m, 2H); 3.19 (s, 3H); 3.41-3.48 (m, 4H); 4.00-4.06 (m, 2H); 7.00-7.11 (m, 2H); 7.22-7.35 (m, 6H); 8.18 (d, J=8.0 Hz, 1H); 8.33 (d, J=0.9 Hz, 1H); 8.49 (d, J=1.7 Hz, 1H); 9.03 (s, 1H); 9.31 (s, 1H); 10.05 (s, 1H)

053: N-[4-Methyl-3-(4-pyridin-3-yl-thiazol-2-ylamino)-phenyl]-4-pyridin-4-yl-benzamide

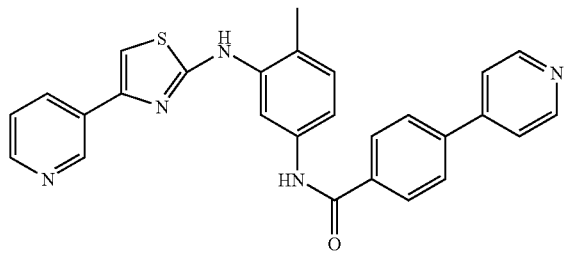

brown powder mp: dec. 250° C. ¹H RMN (DMSO-d⁶) δ=2.28 (s, 3H); 7.21 (d, J=7.9 Hz, 1H); 7.30-7.50 (m, 3H) 7.81 (d, J=4.7 Hz, 1H); 7.98 (d, J=7.5 Hz, 2H); 8.13 (d, J=7.9 Hz, 2H); 8.32 (d, J=7.7 Hz, 1H); 8.48 (d, J=4.9 Hz, 1H); 8.62-8.69 (m, 3H); 9.16 (s, 1H); 9.45 (s, 1H) 10.34 (s, 1H)

054: 3-Cyano-N-[4-methyl-3-(4-pyridin-3-yl-thiazol-2-ylamino)-phenyl]-benzamide

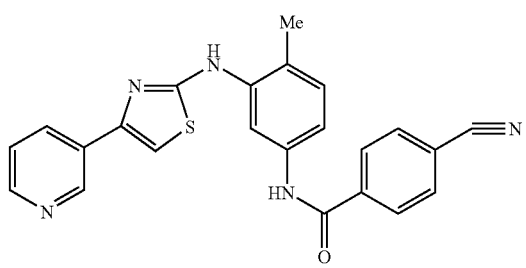

055: 2-Fluoro-N-[4-methyl-3-(4-pyridin-3-yl-thiazol-2-ylamino)-phenyl]-3-trifluoromethyl-benzamide

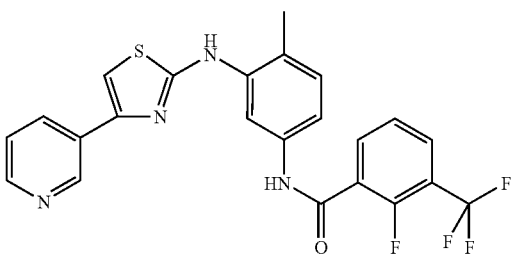

056: 3-Fluoro-benzenesulfonic acid 4-[4-methyl-3-(4-pyridin-3-yl-thiazol-2-ylamino)-phenylcarbamoyl]-phenyl ester

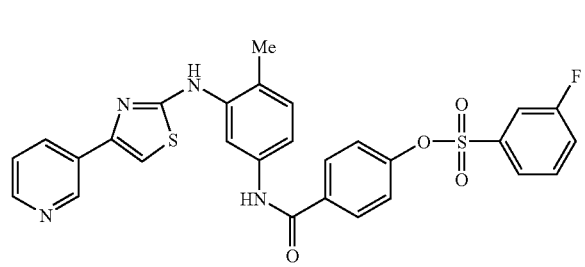

057: 4-Aminomethyl-N-[4-methyl-3-(4-pyridin-3-yl-thiazol-2-ylamino)-phenyl]-benzamide

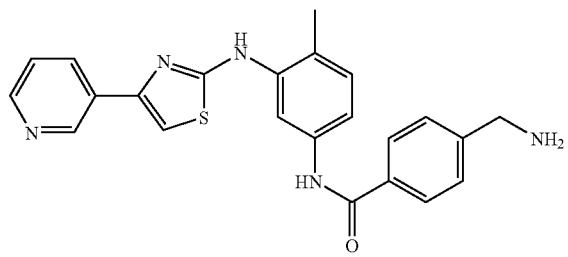

058: 2-Fluoro-benzenesulfonic acid 4-[4-methyl-3-(4-pyridin-3-yl-thiazol-2-ylamino)-phenylcarbamoyl]-phenyl ester

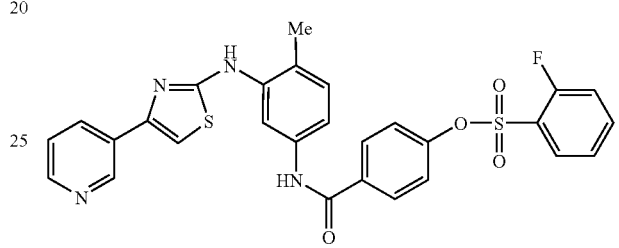

059: 3-Methoxy-N-[4-methyl-3-(4-pyridin-3-yl-thiazol-2-ylamino)-phenyl]-benzamide

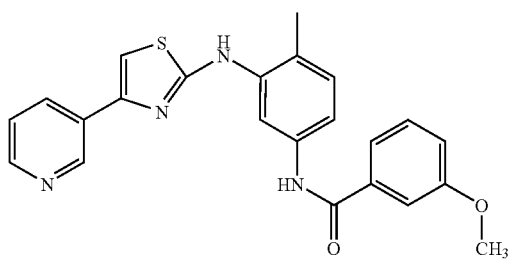

white powder mp: 76-79° C. ¹H RMN (DMSO-d⁶) δ=2.32 (s, 3H); 3.89 (s, 3H); 7.22-7.25 (m, 2H), 7.44-7.58 (m, 4H), 8.28-8.35 (m, 1H); 8.52 (dd, J=1.6 Hz, J=4.7 Hz, 1H); 8.66 (d, J=2.0 Hz, 1H); 9.20 (d, J=1.4 Hz, 1H); 9.50 (s, 1H); 10.25 (s, 1H)

060: 4-(4-Methyl-piperazin-1-yl)-N-[4-methyl-3-(4-pyridin-3-yl-thiazol-2-ylmethyl)-phenyl]-benzamide

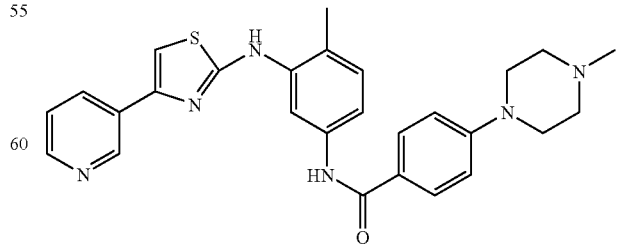

beige brown powder mp: 128-130° C. ¹H RMN (DMSO-d⁶) δ=2.15 (s, 3H); 2.18 (s, 3H); 2.35-2.41 (m, 4H); 3.18-

3.3.24 (m, 4H); 6.94 (d, J=8.9 Hz, 2H); 7.09 (d, J=8.4 Hz, 1H); 7.28-7.38 (m, 3H); 7.81 (d, J=8.9 Hz, 2H); 8.20-8.25 (m, 1H); 8.40 (dd, J=1.6 Hz, J=4.7, 1H); 8.48 (d, J=1.9 Hz, 1H); 9.07 (d, J=1.5 Hz, 1H); 9.35 (s, 1H); 9.84 (s, 1H)

061: 3-Methyl-N-[4-methyl-3-(4-pyridin-3-yl-thiazol-2-ylamino)-phenyl]-benzamide

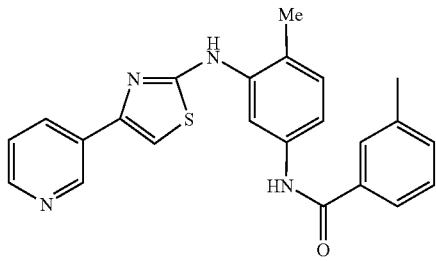

062: Biphenyl-3-carboxylic acid [4-methyl-3-(4-pyridin-3-yl-thiazol-2-ylamino)-phenyl]-amide

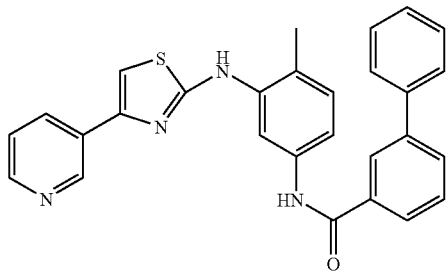

065: N-[4-Methyl-3-(4-pyridin-3-yl-thiazol-2-ylamino)-phenyl]-3-trifluoromethyl-benzamide

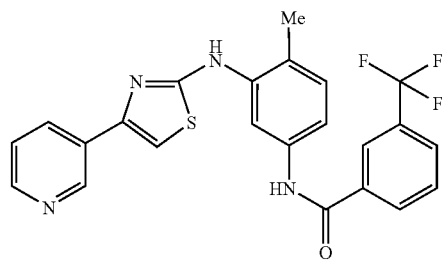

099: N-[4-Methyl-3-(4-pyridin-3-yl-thiazol-2-ylamino)-phenyl]-4-pyrrolidin-1-ylmethyl-benzamide

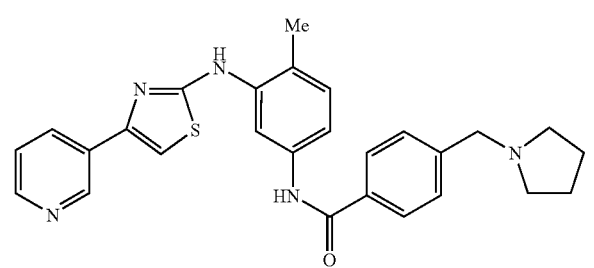

100: 4-[3-(2,4-Dimethoxy-phenyl)-ureido]-N-[4-methyl-3-(4-pyridin-3-yl-thiazol-2-ylamino)-phenyl]-benzamide

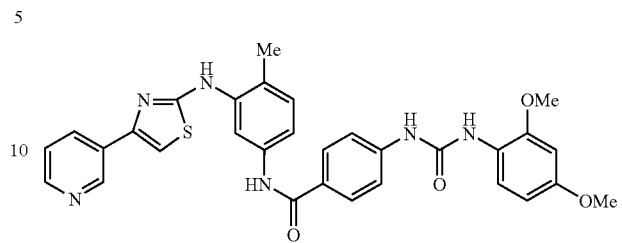

101: 4-[3-(2-Iodo-phenyl)-ureido]-N-[4-methyl-3-(4-pyridin-3-yl-thiazol-2-ylamino)-phenyl]-benzamide

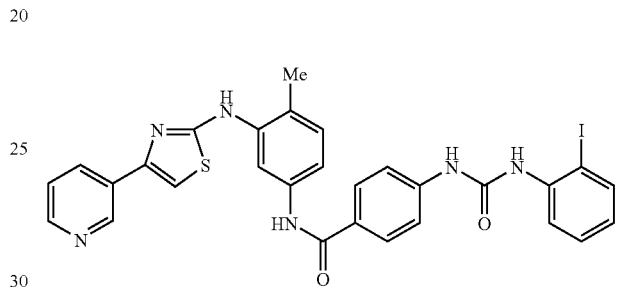

102: 4-[3-(4-Fluoro-phenyl)-ureido]-N-[4-methyl-3-(4-pyridin-3-yl-thiazol-2-ylamino)-phenyl]-benzamide

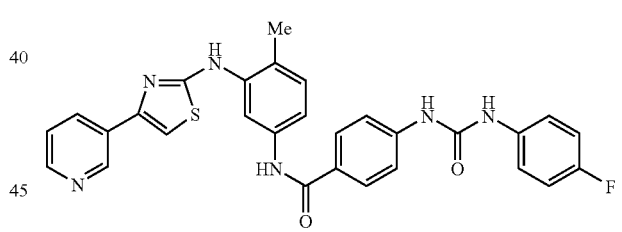

105: 3-Bromo-4-methyl-N-[4-methyl-3-(4-pyridin-3-yl-thiazol-2-ylamino)-phenyl]-benzamide

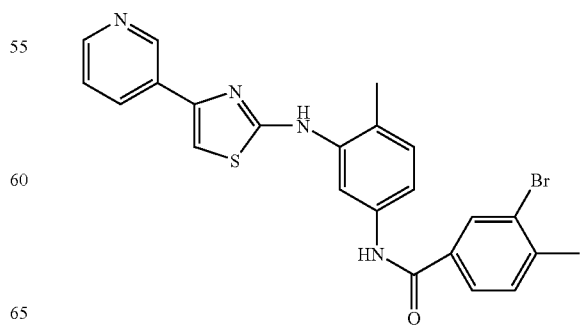

106: 4-Fluoro-N-[4-methyl-3-(4-pyridin-3-yl-thiazol-2-ylamino)-phenyl]-benzamide

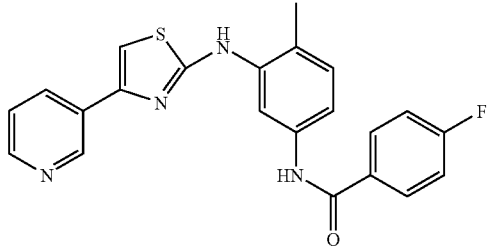

103: 4-Cyano-N-[4-methyl-3-(4-pyridin-3-yl-thiazol-2-ylamino)-phenyl]-benzamide

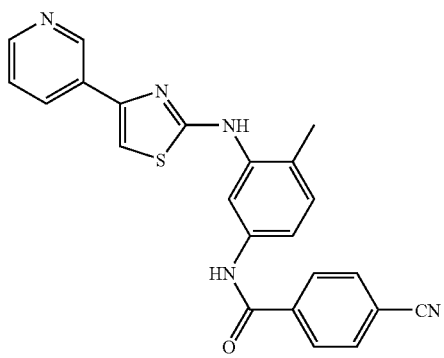

104: 4-Fluoro-N-[4-methyl-3-(4-pyridin-3-yl-thiazol-2-ylamino)-phenyl]-benzamide

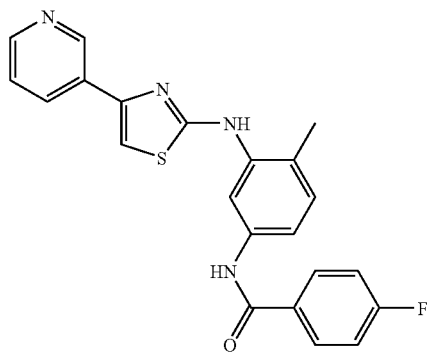

Among compounds of formula II, the invention is particularly embodied by the compounds wherein X is a-substituted-aryl group, corresponding to the 4-(4-substituted-1-ylmethyl)-N-[3-(thiazol-2-ylamino)-phenyl]-benzamide family and the following formula II-4:

FORMULA II-4

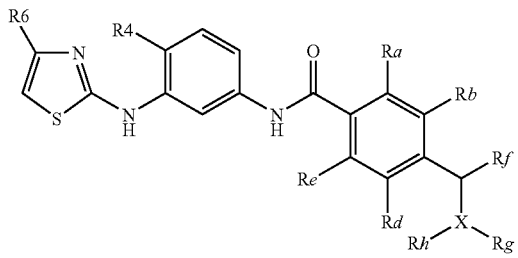

wherein X is a heteroatom, such as O or N wherein Ra, Rb, Rd, Re, Rf, Rg, Rh are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;

or a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a COOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a CONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an NHCOOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and I or bearing a pendant basic nitrogen functionality;

an $OSO_2R$, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an $NRaOSO_2Rb$, where Ra and Rb are a linear or branched alkyl group containing from 1 to 10 carbon atoms atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Ra, Rb, Rd, Re can also be halogen such as Cl, F, Br, I or trifluoromethyl;

$R^4$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

iv) H, a halogen selected from I, F, Cl or Br; NH2, NO2 or SO2-R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality.

EXAMPLES

066: 4-(4-methyl-piperazin-1-ylmethyl)-N-[4-methyl-3-(4-pyridin-3-yl-thiazol-2-ylamino)-phenyl]-benzamide

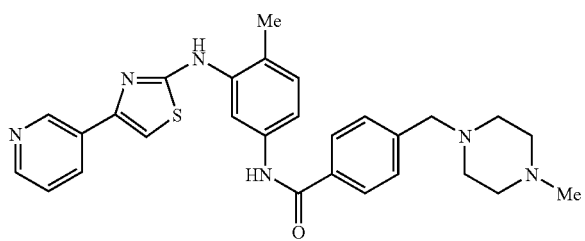

067: 3,5-Dibromo-4-(4-methyl-piperazin-1-ylmethyl)-N-[4-methyl-3-(4-pyridin-3-yl-thiazol-2-ylamino)-phenyl]-benzamide

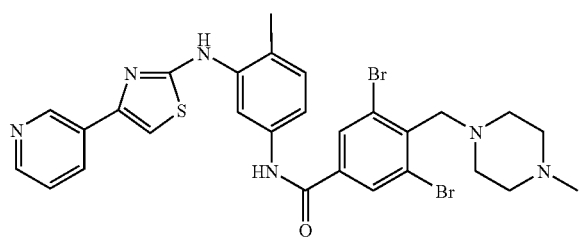

068: 4-Diethylaminomethyl-N-[4-methyl-3-(4-pyridin-3-yl-thiazol-2-ylamino)-phenyl]-benzamide

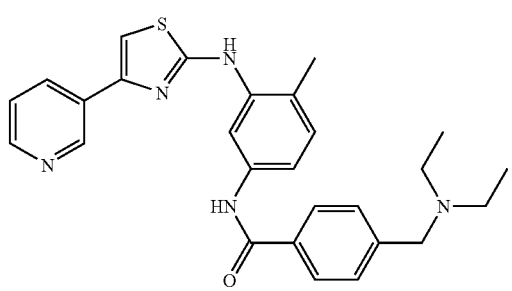

069: N-[4-Methyl-3-(4-pyridin-3-yl-thiazol-2-ylamino)-phenyl]-4-morpholin-4-ylmethyl-benzamide

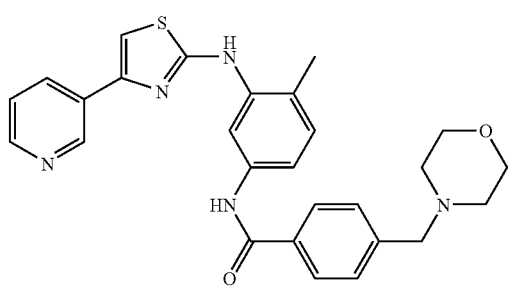

070: 4-Dipropylaminomethyl-N-[4-methyl-3-(4-pyridin-3-yl-thiazol-2-ylamino)-phenyl]-benzamide

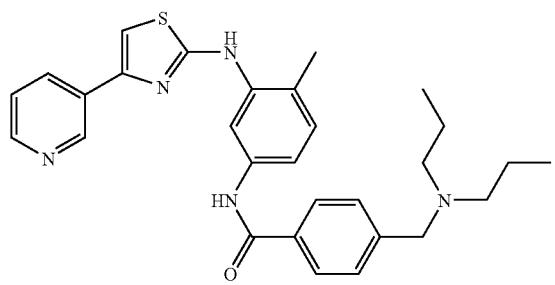

071: N-[4-Methyl-3-(4-pyridin-3-yl-thiazol-2-ylamino)-phenyl]-4-piperidin-1-ylmethyl-benzamide

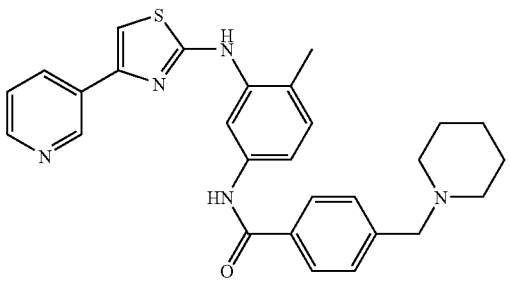

072: 4-[(Diisopropylamino)-methyl]-N-[4-methyl-3-(4-pyridin-3-yl-thiazol-2-ylamino)-phenyl]-benzamide

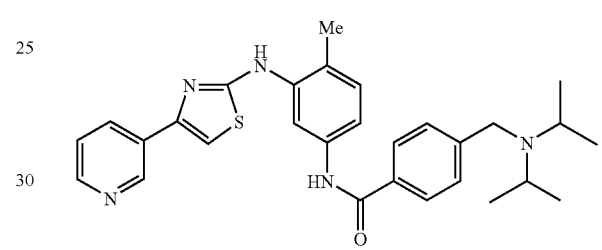

073: {4-[4-Methyl-3-(4-pyridin-3-yl-thiazol-2-ylamino)-phenylcarbamoyl]-benzyl}-carbamic acid tert-butyl ester

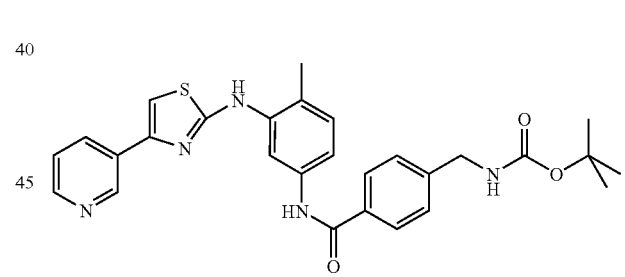

074: 3-Fluoro-4-(4-methyl-piperazin-1-ylmethyl)-N-[4-methyl-3-(4-pyridin-3-yl-thiazol-2-ylamino)-phenyl]-benzamide

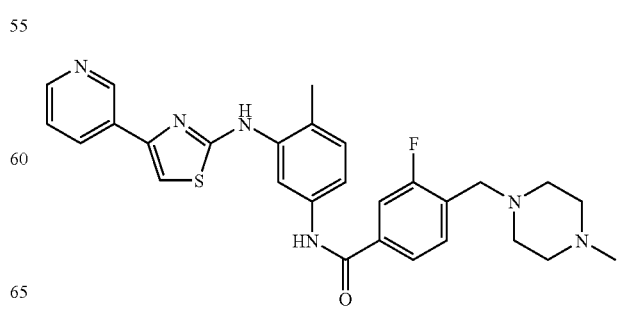

075: 4-(4-Methyl-piperazin-1-ylmethyl)-N-[4-methyl-3-(4-pyridin-3-yl-thiazol-2-ylamino)-phenyl]-3-trifluoromethyl-benzamide

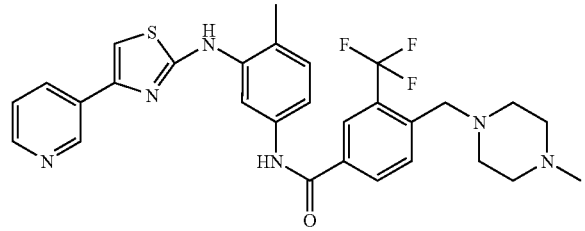

yellow crystals mp: 118-120° C. $^1$H RMN (DMSO-d$^6$) δ=2.22 (s, 3H); 2.33 (s, 3H); 2.34-2.50 (m, 8H); 3.74 (s, 2H); 7.26 (d, J=8.3 Hz, 1H); 7.41-7.49 (m, 2H); 7.53 (s, 1H); 7.99 (d, J=8.0 Hz, 1H); 8.28-8.31 (m, 2H); 8.38 (d, J=7.9 Hz, 1H); 8.53 (dd, J=1.3 Hz, J=4.7 Hz, 1H); 8.68 (d, J=1.9 Hz, 1H); 9.21 (d, J=2.0 Hz, 1H); 9.53 (s, 1H); 10.49 (s, 1H)

076: 2,3,5,6-Tetrafluoro-4-(4-methyl-piperazin-1-ylmethyl)-N-[4-methyl-3-(4-pyridin-3-yl-thiazol-2-ylamino)-phenyl]-benzamide

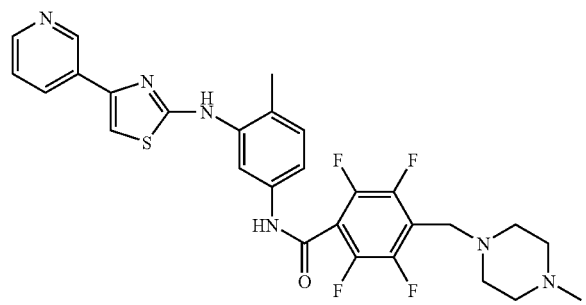

077: N-{3-[4-(4-Fluoro-phenyl)-thiazol-2-ylamino]-4-methyl-phenyl}-4-(4-methyl-piperazin-1-ylmethyl)-benzamide

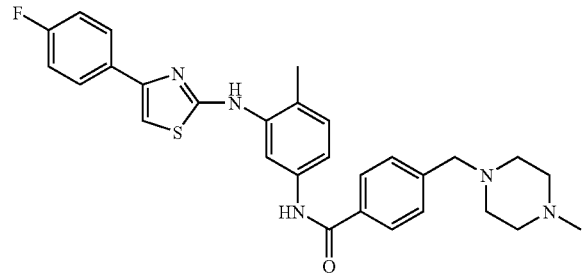

078: 3-Bromo-4-(4-methyl-piperazin-1-ylmethyl)-N-[4-methyl-3-(4-pyridin-3-yl-thiazol-2-ylamino)-phenyl]-benzamide

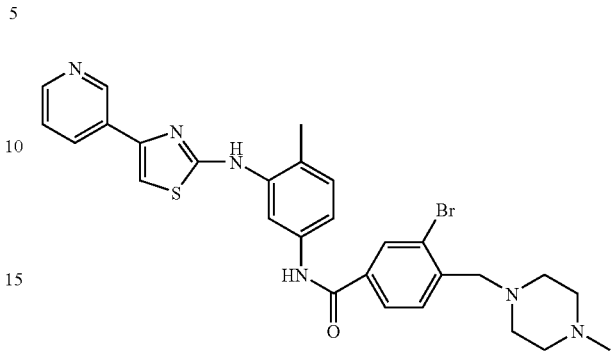

079: 3-Chloro-4-(4-methyl-piperazin-1-ylmethyl)-N-[4-methyl-3-(4-pyridin-3-yl-thiazol-2-ylamino)-phenyl]-benzamide

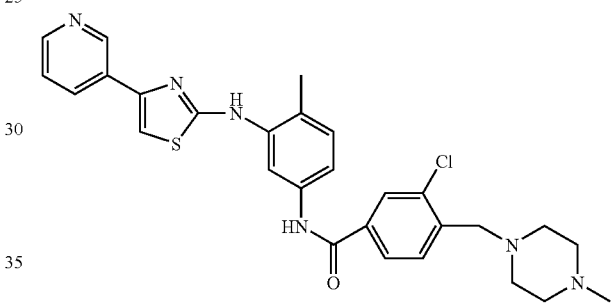

080: 4-(4-Methyl-piperazin-1-ylmethyl)-N-[4-methyl-3-(4-pyridin-4-yl-thiazol-2-ylamino)-phenyl]-benzamide

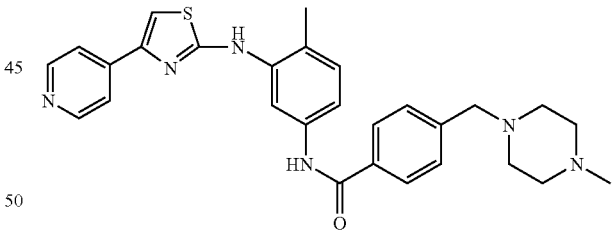

081: N-{3-[4-(4-Cyano-phenyl)-thiazol-2-ylamino]-4-methyl-phenyl}-4-(4-methyl-piperazin-1-ylmethyl)-benzamide

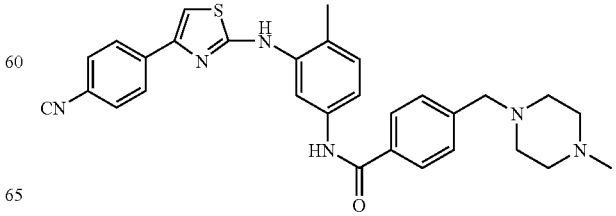

082: 4-[1-(4-Methyl-piperazin-1-yl)-ethyl]-N-[4-methyl-3-(4-pyridin-3-yl-thiazol-2-ylamino)-phenyl]-benzamide 086: N-[4-Methyl-3-(4-pyridin-3-yl-thiazol-2-ylamino)-phenyl]-4-[3-(4-trifluoromethyl-phenyl)-ureidomethyl]-benzamide

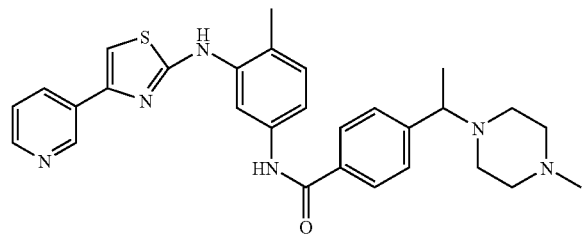

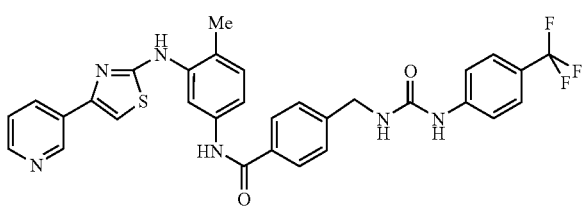

beige powder mp: 153-155° C. $^1$H RMN (DMSO-d$^6$) δ=1.29 (d, J=6.6 Hz, 3H); 2.15 (s, 3H); 2.26 (s, 3H); 3.15-3.25 (m, 9H); 7.18 (d, J=8.4 Hz, 1H); 7.35-7.47 (m, 5H); 7.91 (d, J=8.2 Hz, 2H); 8.31 (d, J=8.0 Hz, 1H); 8.47 (dd, J=1.6 Hz, J=4.7 Hz, 1H); 8.60 (d, J=2.0 Hz, 1H); 9.15 (d, J=0.6 Hz, 1H); 9.45 (s, 1H); 10.18 (s, 1H)

083: 4-(1-Methoxy-ethyl)-N-[4-methyl-3-(4-pyridin-3-yl-thiazol-2-ylamino)-phenyl]-benzamide 087: 3,5-Dibromo-N-[4-methyl-3-(4-pyridin-3-yl-thiazol-2-ylamino)-phenyl]-4-[(3-morpholin-4-yl-propylamino)-methyl]-benzamide

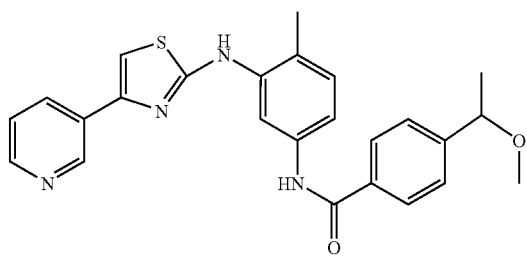

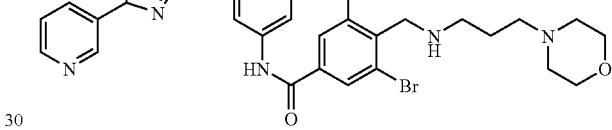

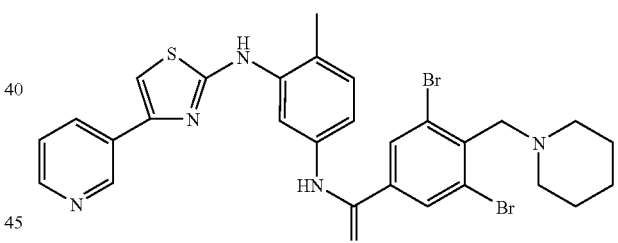

107: 3,5-Dibromo-N-[4-methyl-3-(4-pyridin-3-yl-thiazol-2-ylamino)-phenyl]-4-piperidin-1-ylmethyl-benzamide 084: N-{4-Methyl-3-[4-(5-methyl-pyridin-3-yl)-thiazol-2-ylamino]-phenyl}-4-(4-methyl-piperazin-1-ylmethyl)-benzamide

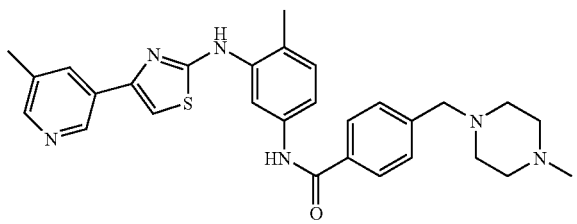

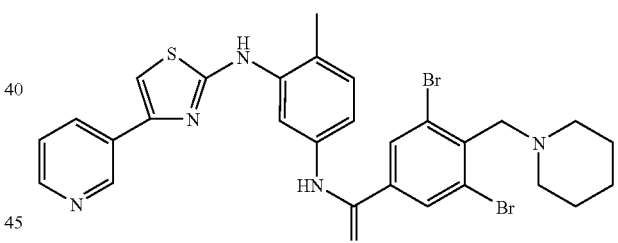

122: 4-(4-Methyl-piperazin-1-ylmethyl)-N-[4-methyl-3-(4-pyridin-2-yl-thiazol-2-ylamino)-phenyl]-benzamide 085: 3-Iodo-4-(4-methyl-piperazin-1-ylmethyl)-N-[4-methyl-3-(4-pyridin-3-yl-thiazol-2-ylamino)-phenyl]-benzamide

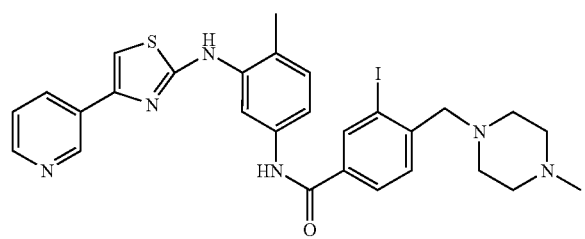

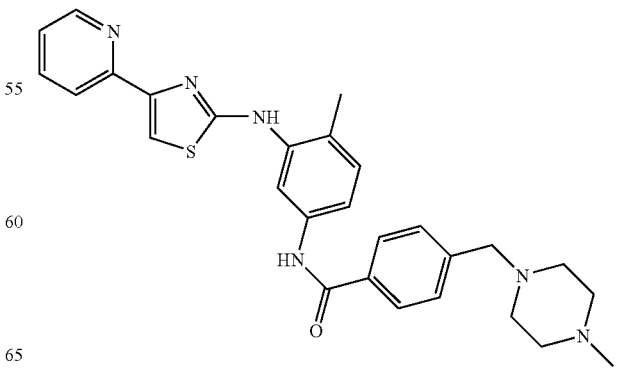

111: N-{3-[4-(3-Fluoro-phenyl)-thiazol-2-ylamino]-4-methyl-phenyl}-4-(4-methyl-piperazin-1-ylmethyl)-benzamide

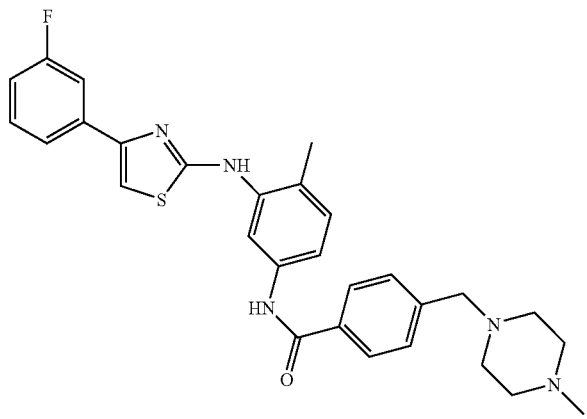

118: N-{3-[4-(2-Fluoro-phenyl)-thiazol-2-ylamino]-4-methyl-phenyl}-4-(4-methyl-piperazin-1-ylmethyl)-benzamides

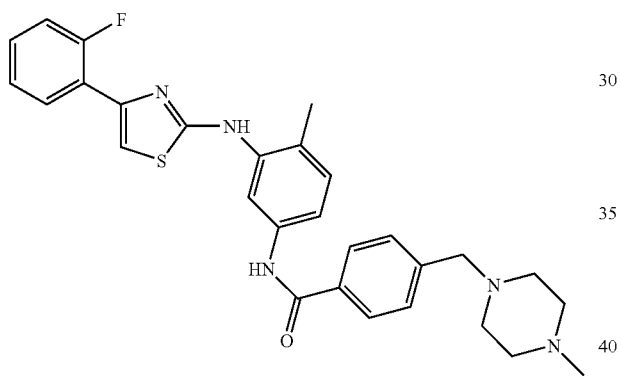

Among compounds of formula II, the invention is particularly embodied by the compounds wherein X is a-aryl-substituted group, corresponding to the 3-Disubstituted-amino-N-[3-(thiazol-2-ylamino)-phenyl]-benzamide family and the following formula II-5:

FORMULA II-5

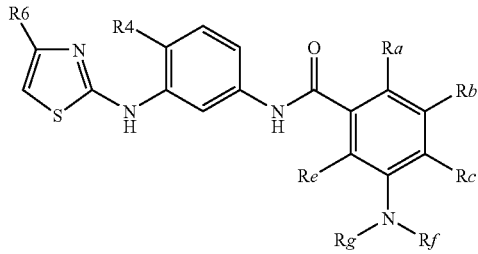

wherein Ra, Rb, Rc, Re, Rf, Rg are independently chosen from H or an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRR' group where R and R' are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or an OR group where R is H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality; a —SO2-R' group wherein R' is an alkyl, cycloalkyl, aryl or heteroaryl optionally substituted with a heteroatom, notably a halogen selected from I, Cl, Br and F or bearing a pendant basic nitrogen functionality;

or a NRaCORb group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a NRaCONRbRc group where Ra and Rb are H or a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with a heteroatom, notably a halogen selected from I, Cl, Br and F or bearing a pendant basic nitrogen functionality; or a cycloalkyl, an aryl or heteroaryl group optionally substituted with a cycloalkyl, an aryl or heteroaryl group optionally substituted with an heteroatom, notably a halogen selected from I, Cl, Br and F or bearing a pendant basic nitrogen functionality;

or a COOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a CONRaRb, where Ra and Rb are a hydrogen or a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an NHCOOR, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

an $OSO_2R$, where R is a linear or branched alkyl group containing from 1 to 10 carbon atoms atoms optionally substituted with at least one heteroatom (for example a halogen) and/or bearing a pendant basic nitrogen functionality; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or an $NRaOSO_2Rb$, where Ra and Rb are a linear or branched alkyl group containing from 1 to 10 carbon atoms atoms optionally substituted with at least one heteroatom (for example a halogen) and/or bearing a pendant basic nitrogen functionality; Ra can also be a hydrogen; a cycloalkyl, an aryl or heteroaryl group optionally substituted with at least one heteroatom, notably a halogen selected from I, Cl, Br and F, and/or bearing a pendant basic nitrogen functionality; or a cycloalkyl, an aryl or heteroaryl group substituted by an alkyl, a cycloalkyl, an aryl or heteroaryl group optionally substituted with an heteroatom, notably a halogen selected from I, Cl, Br and F, and/or bearing a pendant basic nitrogen functionality;

or a —SO2-R group wherein R is an alkyl, cycloalkyl, aryl or heteroaryl optionally substituted with an heteroatom, notably a halogen selected from I, Cl, Br and F or bearing a pendant basic nitrogen functionality; or a —CO—R or a —CO—NRR' group, wherein R and R' are independently chosen from H, an alkyl, a cycloalkyl, an aryl or heteroaryl group optionally substituted with at least one heteroatom, notably selected from I, Cl, Br and F, and/or bearing a pendant basic nitrogen functionality.

Ra, Rb, Rc, Re can also be halogen such as Cl, F, Br, I or trifluoromethyl;

$R^4$ is hydrogen, halogen or a linear or branched alkyl group containing from 1 to 10 carbon atoms, trifluoromethyl or alkoxy;

$R^6$ is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;
(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;
iv) H, a halogen selected from 1, F, Cl or Br; NH2, NO2 or SO2-R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality.

EXAMPLES

088: 3-Dimethylamino-N-[4-methyl-3-(4-pyridin-3-yl-thiazol-2-ylamino)-phenyl]-benzamide

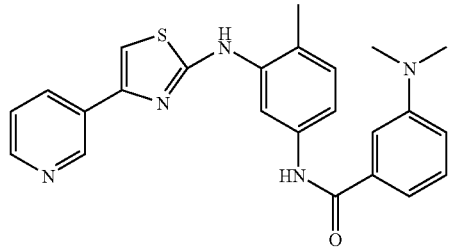

beige powder mp: 197-198° C. $^1$H NMR (DMSO-d$^6$): δ=2.32 (s, 3H); 3.03 (s, 6H); 6.97 (d, J=6.4 Hz, 1H); 7.23-7.56 (m, 7H); 8.37 (d, J=7.3 Hz, 1H); 8.53 (d, J=4.7 Hz, 1H); 8.63 (s, 1H); 9.20 (s, 1H); 9.48 (s, 1H); 10.15 (s, 1H)

089: 3-(4-Methyl-piperazin-1-yl)-N-[4-methyl-3-(4-pyridin-3-yl-thiazol-2-ylamino)-phenyl]-benzamide

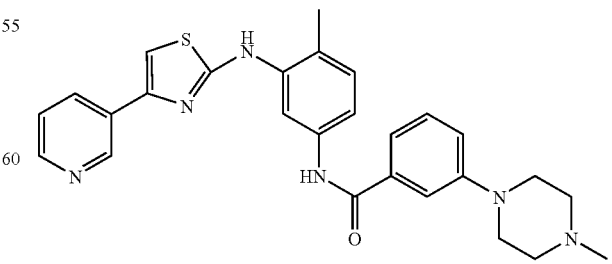

beige powder mp: 274-246° C. $^1$H RMN (DMSO-d$^6$) δ=2.23 (s, 3H); 2.24-2.30 (m, 4H); 3.22-3.27 (m, 4H); 7.07-

7.20 (m, 2H); 7.36-7.53 (m, 6H); 8.31 (d, J=7.5 Hz, 1H); 8.47 (d, J=3.7 Hz, 1H) 8.58 (s, 1H); 9.12 (d, J=7.8 Hz, 1H); 9.44 (s, 1H); 10.12 (s, 1H)

090: N-[4-Methyl-3-(4-pyridin-3-yl-thiazol-2-ylamino)-phenyl]-3-morpholin-4-yl-benzamide

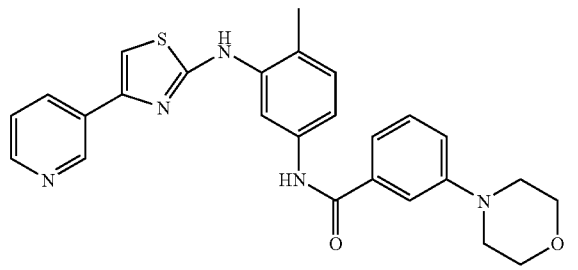

beige powder mp: 247-248° C. $^1$H RMN (CDCl$_3$) δ=1.50 (s, 3H); 3.15-3.18 (m, 4H); 3.79-3.82 (m, 3H); 6.85 (s, 1H); 7.00-7.30 (m, 7H); 7.41 (s, 1H); 7.75 (s, 1H); 8.08 (d, J=7.9 Hz, 1H); 8.22 (d, J=1.7 Hz, 1H); 8.46 (dd, J=1.3 Hz, J=4.7 Hz, 1H); 9.01 (d, J=1.6 Hz, 1H)

Among the compounds of formula II, the invention is particularly embodied by the compounds wherein X is a —OR group, corresponding to the family [3-(Thiazol-2-ylamino)-phenyl]-carbamate and the following formula II-6

FORMULA II-6

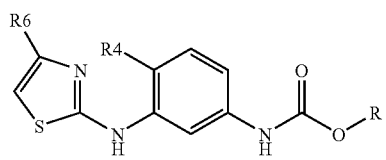

wherein R is independently chosen from an organic group that can be selected for example from a linear or branched alkyl group containing from 1 to 10 carbon atoms optionally substituted with at least one heteroatom and/or bearing a pendant basic nitrogen functionality; a cycloalkyl, an aryl or heteroaryl group optionally substituted with an heteroatom, notably a halogen selected from I, Cl, Br and F and/or bearing a pendant basic nitrogen functionality; or a cycloalkyl, an aryl or heteroaryl group optionally substituted with a cycloalkyl, an aryl or heteroaryl group optionally substituted with a heteroatom, notably a halogen selected from I, Cl, Br and F and/or bearing a pendant basic nitrogen functionality;

$R^4$ is hydrogen, halogen or a linear or branched alkyl group containing from 1 to 10 carbon atoms, trifluoromethyl or alkoxy;

$R^6$ is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, and alkoxy;

(ii) a heteroaryl group such as a 2,3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy;

iv) H, a halogen selected from 1, F, Cl or Br; NH2, NO2 or SO2-R, wherein R is a linear or branched alkyl goup containing one or more group such as 1 to 10 carbon atoms, and optionally substituted with at least one heteroatom, notably a halogen selected from I, Cl, Br and F, and/or bearing a pendant basic nitrogen functionality.

EXAMPLES

097: [4-Methyl-3-(4-pyridin-3-yl-thiazol-2-ylamino)-phenyl]-carbamic acid isobutyl ester

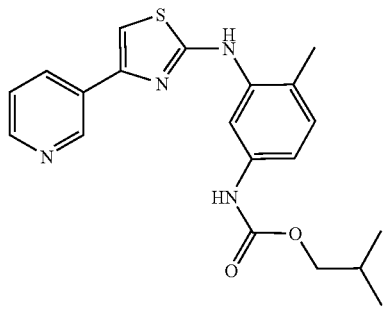

098: [4-Methyl-3-(4-pyridin-3-yl-thiazol-2-ylamino)-phenyl]-carbamic acid tert-butyl ester

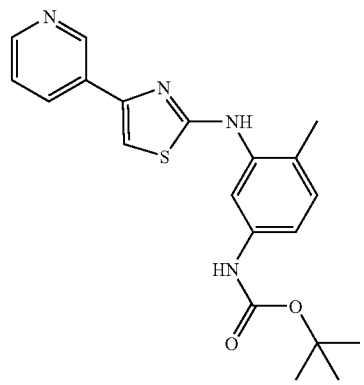

In a second embodiment, the invention is directed to a process for manufacturing a compound of formula I depicted above. This entails the condensation of a substrate of general formula 10 with a thiourea of the type 11a-11d.

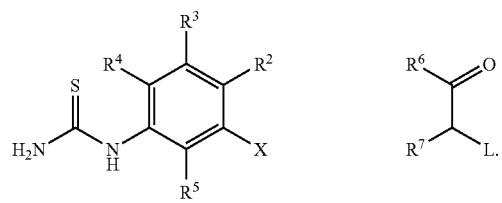

11 a: X = NH—R$^1$
11 b: X = NH$_2$
11 c: X = NH—PG
11 b: X = NO$_2$

Substituent "L" in formula 10 is a leaving group suitable in nucleophilic substitution reactions (for example, L can be selected from chloro, bromo, iodo, toluenesulfonyloxy, methanesulfonyloxy, trifluoromethanesulfonyloxy, etc., with L being preferentially a bromo group).

Group R1 in formula 11a corresponds to group R1 as described in formula I.

Group "PG" in formula 11c is a suitable protecting group of a type commonly utilized by the person skilled in the art.

The reaction of 10 with 1 a-d leads to a thiozole-type product of formula 12a-d.

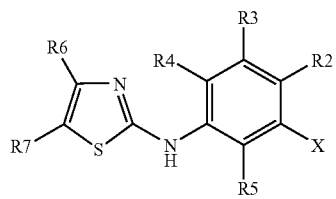

12 a: X = NH—R1
12 b: X = NH2
12 c: X = NH—PG
12 d: X = NO2

Formula 12a is the same as formula I. Therefore, R1 in 12a corresponds to R1 in formula I.

Formula 12b describes a precursor to compounds of formula I which lack substituent R1. Therefore, in a second phase of the synthesis, substituent R1 is connected to the free amine group in 12b, leading to the complete structure embodied by formula I:

12b+"R1"→I

The introduction of R1, the nature of which is as described on page 3 for the general formula I, is achieved by the use of standard reactions that are well known to the person skilled in the art, such as alkylation, acylation, sulfonylation, formation of ureas, etc.

Formula 12c describes an N-protected variant of compound 12b. Group "PG" in formula 12c represents a protecting group of the type commonly utilized by the person skilled in the art. Therefore, in a second phase of the synthesis, group PG is cleaved to transform compound 12c into compound 12b. Compound 12b is subsequently advanced to structures of formula I as detailed above.

Formula 12d describes a nitro analogue of compound 12b. In a second phase of the synthesis, the nitro group of compound 12d is reduced by any of the several methods utilized by the person skilled in the art to produce the corresponding amino group, namely compound 12b. Compound 12b thus obtained is subsequently advanced to structures of formula I as detailed above.

Examples of Compound Synthesis

General: All chemicals used were commercial reagent grade products. Dimethylformamide (DMF), methanol (MeOH) were of anhydrous commercial grade and were used without further purification. Dichloromethane and tetrahydrofuran (THF) were freshly distilled under a stream of argon before use. The progress of the reactions was monitored by thin layer chromatography using precoated silica gel 60F 254, Fluka TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were realized on a 300 MHz Bruker spectrometer.

3-Bromoacetyl-pyridine, HBr Salt

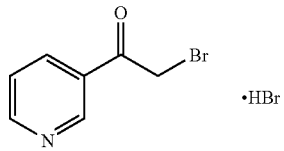

Dibromine (17.2 g, 108 mmol) was added dropwise to a cold (0° C.) solution of 3-acetyl-pyridine (12 g, 99 mmol) in acetic acid containing 33% of HBr (165 mL) under vigourous stirring. The vigorously stirred mixture was warmed to 40° C. for 2 h and then to 75° C. After 2 h at 75° C., the mixture was cooled and diluted with ether (400 mL) to precipitate the product, which was recovered by filtration and washed with ether and acetone to give white crystals (100%). This material may be recrystallised from methanol and ether.

IR (neat): 3108, 2047, 2982, 2559, 1709, 1603, 1221, 1035, 798 cm$^{-1}$—$^1$H NMR (DMSO-d$^6$) δ=5.09 (s, 2H, CH$_2$Br); 7.88 (m, 1H, pyridyl-H); 8.63 (m, 1H, pyridyl-H); 8.96 (m, 1H, pyridyl-H); 9.29 (m, 1H, pyridyl-H).

Methyl-[4-(1-N-methyl-piperazino)-methyl]-benzoate

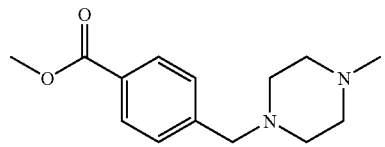

To methyl-4-formyl benzoate (4.92 g, 30 mmol) and N-methyl-piperazine (3.6 mL, 32 mmol) in acetonitrile (100 mL) was added dropwise 2.5 mL of trifluoroacetic acid. The reaction mixture was stirred at room temperature for 1 h. After slow addition of sodium cyanoborohydride (2 g, 32 mmol), the solution was left stirring overnight at room temperature. Water (10 mL) was then added to the mixture, which was further acidified with 1N HCl to pH=6-7. The acetonitrile was removed under reduced pressure and the residual aqueous solution was extracted with diethyl ether (4×30 mL). These extracts were discarded. The aqueous phase was then basified (pH>12) by addition of 2.5N aqueous sodium hydroxyde solution. The crude product was extracted with ethyl acetate (4×30 mL). The combined organic layers were dried over MgSO$_4$ and concentrated under reduced pressure to afford a slightly yellow oil which became colorless after purification by Kugelrohr distillation (190° C.) in 68% yield.

IR(neat): 3322, 2944, 2802, 1721, 1612, 1457, 1281, 1122, 1012—$^1$H NMR(CDCl$_3$) δ=2.27 (s, 3H, NCH$_3$); 2.44 (m, 8H, 2×NCH$_2$CH$_2$N); 3.53 (s, 2H, ArCH$_2$N); 3.88 (s, 3H, OCH$_3$); 7.40 (d, 2H, J=8.3 Hz, 2×ArH); 7.91 (d, 2H, J=8.3 Hz, 2×ArH)—$^{13}$C NMR (CDCl$_3$) δ=45.8 (NCH$_3$); 51.8 (OCH$_3$); 52.9 (2×CH$_2$N); 54.9 (2×CH$_2$N); 62.4 (ArCH$_2$N); 128.7 (2×ArC); 129.3 (2×ArC); 143.7 (ArC); 166.7 (ArCO$_2$CH$_3$)- MS CI (m/z) (%) 249 (M+1, 100%).

2-Methyl-5-tert-butoxycarbonylamino-aniline

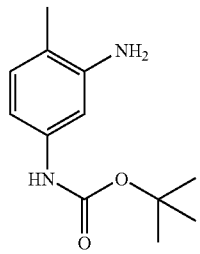

A solution of di-tert-butyldicarbonate (70 g, 320 mmol) in methanol (200 mL) was added over 2 h to a cold (−10° C.) solution of 2,4-diaminotoluene (30 g, 245 mmol) and triethylamine (30 mL) in methanol (15 mL). The reaction was followed by thin layer chromatography (hexane/ethyl acetate, 3:1) and stopped after 4 h by adding 50 mL of water. The mixture was concentrated in vacuo and the residue was dissolved in 500 mL of ethyl acetate. This organic phase was washed with water (1×150 mL) and brine (2×150 mL), dried over MgSO$_4$, and concentrated under reduced pressure. The resulting light brown solid was washed with small amounts of diethyl ether to give off-white crystals of 2-methyl-5-tert-butoxycarbonylamino-aniline in 67% yield.

IR (neat): 3359; 3246; 2970; 1719; 1609; 1557; 1173; 1050 cm$^{-1}$—$^1$H NMR (CDCl$_3$): δ=1.50 (s, 9H, tBu); 2.10 (s, 3H, ArCH$_3$); 3.61 (br s, 2H, NH$_2$); 6.36 (br s, 1H, NH); 6.51 (dd, 1H, J=7.9 Hz, 2.3 Hz, ArH); 6.92 (d, 1H, J=7.9 Hz, ArH); 6.95 (s, 1H, ArH)—$^{13}$C NMR (CDCl$_3$) δ=16.6 (ArCH$_3$); 28.3 (C(CH$_3$)$_3$); 80.0 (C(CH$_3$)$_3$); 105.2 (ArC); 108.6 (ArC); 116.9 (ArC); 130.4 (ArC—CH$_3$); 137.2 (ArC—NH); 145.0 (ArC—NH$_2$); 152.8 (COOtBu) MS ESI (m/z) (%): 223 (M+1), 167 (55, 100%).

N-(2-methyl-5-tert-butoxycarbonylamino)phenyl-thiourea

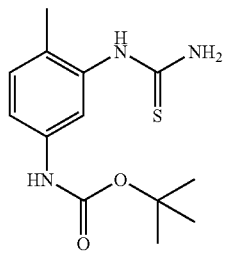

Benzoyl chloride (5.64 g, 80 mmol) was added dropwise to a well-stirred solution of ammonium thiocyanate (3.54 g, 88 mmol) in acetone (50 mL). The mixture was refluxed for 15 min, then, the hydrobromide salt of 2-methyl-5-tert-butoxycarbonylamino-aniline (8.4 g, 80 mmol) was added slowly portionswise. After 1 h, the reaction mixture was poured into ice-water (350 mL) and the bright yellow precipitate was isolated by filtration. This crude solid was then refluxed for 45 min in 70 mL of 2.5 N sodium hydroxide solution. The mixture was cooled down and basified with ammonium hydroxide. The precipitate of crude thiourea was recovered by filtration and dissolved in 150 mL of ethyl acetate. The organic phase was washed with brine, dried over Na$_2$SO$_4$, and concentrated under reduced pressure. The residue was purified by column chromatography (hexane/ethyl acetate, 1:1) to afford 63% of N-(2-methyl-5-tert-butoxycarbonylamino) phenyl-thiourea as a white solid.

IR (neat): 3437, 3292, 3175, 2983, 1724, 1616, 1522, 1161, 1053 cm$^{-1}$—$^1$H NMR (DMSO-d$_6$) δ=1.46 (s, 9H, tBu); 2.10 (s, 3H, ArCH$_3$); 3.60 (br s, 2H, NH$_2$); 7.10 (d, 1H, J=8.29 Hz, ArH); 7.25 (d, 1H, J=2.23 Hz, ArH); 7.28 (d, 1H, J=2.63 Hz, ArH); 9.20 (s, 1H, ArNH); 9.31 (s, 1H, ArNH)—$^{13}$C NMR (DMSO-d$^6$) δ=25.1 (ArCH$_3$); 28.1 (C(CH$_3$)$_3$); 78.9 (C(CH$_3$)$_3$); 16.6 (ArC); 117.5 (ArC); 128.0 (ArC); 130.4 (ArC—CH$_3$); 136.5 (ArC—NH); 137.9 (ArC—NH); 152.7 (COOtBu); 181.4 (C=S)—MS CI(m/z): 282 (M+1, 100%); 248 (33); 226 (55); 182 (99); 148 (133); 93 (188).

2-(2-methyl-5-tert-butoxycarbonylamino)phenyl-4-(3-pyridyl)-thiazole

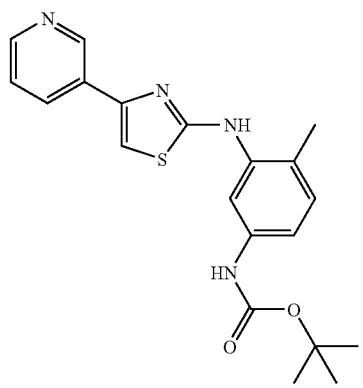

A mixture of 3-bromoacetyl-pyridine, HBr salt (0.81 g, 2.85 mmol), N-(2-methyl-5-tert-butoxycarbonylamino)phenyl-thiourea (0.8 g, 2.85 mmol) and KHCO$_3$ (~0.4 g) in ethanol (40 mL) was heated at 75° C. for 20 h. The mixture was cooled, filtered (removal of KHCO$_3$) and evaporated under reduced pressure. The residue was dissolved in CHCl$_3$ (40 mL) and washed with saturated aqueous sodium hydrogen carbonate solution and with water. The organic layer was dried over Na$_2$SO$_4$ and concentrated. Colum chromatographic purification of the residue (hexane/ethyl acetate, 1:1) gave the desired thiazole in 70% yield as an orange solid IR(neat): 3380, 2985, 2942, 1748, 1447, 1374, 1239, 1047, 938—$^1$H NMR (CDCl$_3$) δ=1.53 (s, 9H, tBu); 2.28 (s, 3H, ArCH$_3$); 6.65 (s, 1H, thiazole-H); 6.89 (s, 1H); 6.99 (dd, 1H, J=8.3 Hz, 2.3 Hz); 7.12 (d, 2H, J=8.3 Hz); 7.35 (dd, 1H, J=2.6 Hz, 4.9 Hz); 8.03 (s, 1H); 8.19 (dt, 1H, J=1.9 Hz, 7.9 Hz); 8.54 (br s, 1H, NH); 9.09 (s, 1H, NH)—$^{13}$C NMR (CDCl$_3$) δ=18.02 (ArCH$_3$); 29.2 (C(CH$_3$)$_3$); 81.3 (C(CH$_3$)$_3$); 104.2 (thiazole-C); 111.6; 115.2; 123.9; 124.3; 131.4; 132.1; 134.4; 139.5; 148.2; 149.1; 149.3; 153.6; 167.3 (C=O)—MS CI (m/z) (%): 383 (M+1, 100%); 339 (43); 327 (55); 309 (73); 283 (99); 71 (311).

2-(2-methyl-5-amino)phenyl-4-(3-pyridyl)-thiazole

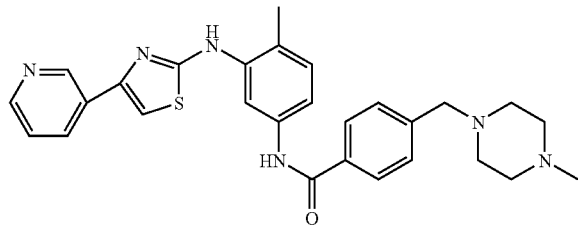

2-(2-methyl-5-tert-butoxycarbonylamino)phenyl-4-(3-pyridyl)-thiazole (0.40 g, 1.2 mmol) was dissolved in 10 mL of 20% TFA/CH$_2$Cl$_2$. The solution was stirred at rool temperature for 2 h, then it was evaporated under reduced pressure. The residue was dissolved in ethyl acetate. The organic layer was washed with aqueous 1N sodium hydroxide solution, dried over MgSO$_4$, and concentrated to afford 2-(2-methyl-5-amino)phenyl-4-(3-pyridyl)-thiazole as a yellow-orange solid in 95% yield. This crude product was used directly in the next step.

A 2M solution of trimethyl aluminium in toluene (2.75 mL) was added dropwise to a cold (0° C.) solution of 2-(2-methyl-5-amino)phenyl-4-(3-pyridyl)-thiazole (0.42 g, 1.5 mmol) in anhydrous dichloromethane (10 mL) under argon atmosphere. The mixture was warmed to room temperature and stirred at room temperature for 30 min. A solution of methyl-4-(1-N-methyl-piperazino)-methyl benzoate (0.45 g, 1.8 mmol) in anhydrous dichloromethane (1 mL) and added slowly, and the resulting mixture was heated at reflux for 5 h. The mixture was cooled to 0° C. and quenched by dropwise addition of a 4N aqueous sodium hydroxide solution (3 mL). The mixture was extracted with dichloromethane (3×20 mL). The combined organic layers were washed with brine (3×20 mL) and dried over anhydrous MgSO$_4$. (2-(2-methyl-5-amino)phenyl-4-(3-pyridyl)-thiazole) is obtained in 72% after purification by column chromatography (dichloromethane/methanol, 3:1)

IR (neat): 3318, 2926, 1647, 1610, 1535, 1492, 1282, 1207, 1160, 1011, 843—$^1$H NMR (CDCl$_3$) δ=2.31 (br s, 6H, ArCH$_3$+NCH$_3$); 2.50 (br s, 8H, 2×NCH$_2$CH$_2$N); 3.56 (s, 2H, ArCH$_2$N); 6.89 (s, 1H, thiazoleH); 7.21-7.38 (m, 4H); 7.45 (m, 2H); 7.85 (d, 2H, J=8.3 Hz); 8.03 (s, 1H); 8.13 (s, 1H); 8.27 (s, 1H); 8.52 (br s, 1H); 9.09 (s, 1H, NH)—$^{13}$C NMR (CDCl$_3$) δ 17.8 (ArCH$_3$); 46.2 (NCH$_3$); 53.3 (NCH$_2$); 55.3 (NCH$_2$); 62.8 (ArCH$_2$N); 99.9 (thiazole-C); 112.5; 123.9; 125.2; 127.5; 129.6; 131.6; 133.7; 134.0; 137.6; 139.3; 142.9; 148.8; 149.1; 166.2 (C=O); 166.7 (thiazoleC-NH)—MS CI (m/z) (%): 499 (M+H, 100%); 455 (43); 430 (68); 401 (97); 374 (124); 309 (189); 283 (215); 235 (263); 121 (377); 99 (399).

In a third embodiment, the invention relates to a pharmaceutical composition comprising a compound as depicted above.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture are contemplated.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor, preferably a c-kit inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art.

For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V.60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biolocy of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (U.S. Pat. Nos. 3,740,420 and 3,743,727, and U.S. Pat. No. 4,575,515), and glycerine derivatives (U.S. Pat. No. 4,322,433) are a few examples of compounds which have shown an ability to enhance the absorption of various compounds.

The pharmaceutical compositions of the invention can also be intended for administration with aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:

liquid gas systems (a liquefied gas is used as propellent gas (e.g. low-boiling FCHC or propane, butane) in a pressure container, suspension aerosol (the active substance particles are suspended in solid form in the liquid propellent phase), pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of said compound to manufacture a medicament. In other words, the invention embraces a method for treating a disease related to unregulated c-kit transduction comprising administering an effective amount of a compound as defined above to a mammal in need of such treatment.

More particularly, the invention is aimed at a method for treating a disease selected from autoimmune diseases, allergic diseases, bone loss, cancers such as leukemia and GIST, tumor angiogenesis, inflammatory diseases, inflammatory bowel diseases (IBD), interstitial cystitis, mastocytosis, infections diseases, metabolic disorders, fibrosis, diabetes and CNS disorders comprising administering an effective amount a compound depicted above to a mammal in need of such treatment.

The above described compounds are useful for manufacturing a medicament for the treatment of diseases related to unregulated c-kit transduction, including, but not limited to:

neoplastic diseases such as mastocytosis, canine mastocytoma, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, solid tumors and astrocytomas.

tumor angiogenesis.

metabolic diseases such as diabetes mellitus and its chronic complications; obesity; diabete type II; hyperlipidemias and dyslipidemias; atherosclerosis; hypertension; and cardiovascular disease.

allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.

interstitial cystitis.

bone loss (osteoporosis).

inflammatory diseases such as rheumatoid arthritis, conjunctivitis, rheumatoid spondylitis, osteoarthritis, gouty arthritis and other arthritic conditions.

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis.

graft-versus-host disease or graft rejection in any organ transplantation including kidney, pancreas, liver, heart, lung, and bone marrow.

Other autoimmune diseases embraced by the invention active chronic hepatitis and chronic fatigue syndrome subepidermal blistering disorders such as pemphigus.

Vasculitis.

melanocyte dysfunction associated diseases such as hypermelanosis resulting from melanocyte dysfunction and including lentigines, solar and senile lentigo, Dubreuilh melanosis, moles as well as malignant melanomas. In this regard, the invention embraces the use of the compounds defined above to manufacture a medicament or a cosmetic composition for whitening human skin.

CNS disorders such as psychiatric disorders, migraine, pain, memory loss and nerve cells degeneracy. More particularly, the method according to the invention is useful for the treatment of the following disorders: Depression including dysthymic disorder, cyclothymic disorder, bipolar depression, severe or "melancholic" depression, a typical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, posttraumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia, neurodegenerative diseases including Alzheimer's disease, Parkinson's disease, Huntington's disease, the prion diseases, Motor Neurone Disease (MND), and Amyotrophic Lateral Sclerosis (ALS).

substance use disorders as referred herein include but are not limited to drug addiction, drug abuse, drug habituation, drug dependence, withdrawal syndrome and overdose.

Cerebral ischemia

Fibrosis

Duchenne muscular dystrophy

Regarding mastocytosis, the invention contemplates the use of the compounds as defined above for treating the different categories which can be classified as follows:

The category I is composed by two sub-categories (IA and IB). Category IA is made by diseases in which mast cell infiltration is strictly localized to the skin. This category represents the most frequent form of the disease and includes: i) urticaria pigmentosa, the most common form of cutaneous mastocytosis, particularly encountered in children, ii) diffuse cutaneous mastocytosis, iii) solitary mastocytoma and iv) some rare subtypes like bullous, erythrodermic and teleangiectatic mastocytosis. These forms are characterized by their excellent prognosis with spontaneous remissions in children and a very indolent course in adults. Long term survival of this form of disease is generally comparable to that of the normal population and the translation into another form of mastocytosis is rare. Category IB is represented by indolent systemic disease (SM) with or without cutaneous involvement. These forms are much more usual in adults than in children. The course of the disease is often indolent, but sometimes signs of aggressive or malignant mastocytosis can occur, leading to progressive impaired organ function.

The category II includes mastocytosis with an associated hematological disorder, such as a myeloproliferative or myelodysplastic syndrome, or acute leukemia. These malignant mastocytosis does not usually involve the skin. The progression of the disease depends generally on the type of associated hematological disorder that conditiones the prognosis.

The category III is represented by aggressive systemic mastocytosis in which massive infiltration of multiple organs by abnormal mast cells is common. In patients who pursue this kind of aggressive clinical course, peripheral blood features suggestive of a myeloproliferative disorder are more prominent. The progression of the disease can be very rapid, similar to acute leukemia, or some patients can show a longer survival time.

Finally, the category IV of mastocytosis includes the mast cell leukemia, characterized by the presence of circulating mast cells and mast cell progenitors representing more than 10% of the white blood cells. This entity represents probably the rarest type of leukemia in humans, and has a very poor prognosis, similar to the rapidly progressing variant of malignant mastocytosis. Mast cell leukemia can occur either de novo or as the terminal phase of urticaria pigmentosa or systemic mastocytosis.

The invention also contemplates the method as depicted for the treatment of recurrent bacterial infections, resurging infections after asymptomatic periods such as bacterial cystitis. More particularly, the invention can be practiced for treating FimH expressing bacteria infections such as Gram-negative enterobacteria including *E. coli, Klebsiella pneumoniae, Serratia marcescens, Citrobacter freudii* and *Salmonella typhimurium*. In this method for treating bacterial infection, separate, sequential or concomitant administration of at least one antibiotic selected bacitracin, the cephalosporins, the penicillins, the aminoglycosides, the tetracyclines, the streptomycins and the macrolide antibiotics such as erythromycin; the fluoroquinolones, actinomycin, the sulfonamides and trimethoprim, is of interest.

In one preferred embodiment, the invention is directed to a method for treating neoplastic diseases such as mastocytosis, canine mastocytoma, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas comprising administering a compound as defined herein to a human or mammal, especially dogs and cats, in need of such treatment.

In one other preferred embodiment, the invention is directed to a method for treating allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation comprising administering a compound as defined herein to a human or mammal, especially dogs and cats, in need of such treatment.

In still another preferred embodiment, the invention is directed to a method for treating inflammatory diseases such as rheumatoid arthritis, conjunctivitis, rheumatoid spondylitis, osteoarthritis, gouty arthritis and other arthritic conditions comprising administering a compound as defined herein to a human in need of such treatment.

In still another preferred embodiment, the invention is directed to a method for treating autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis comprising administering a compound as defined herein to a human in need of such treatment.

In still another preferred embodiment, the invention is directed to a method for treating graft-versus-host disease or graft rejection in any organ transplantation including kidney, pancreas, liver, heart, lung, and bone marrow comprising administering a compound as defined herein to a human in need of such treatment.

Example 1

In Vitro TK Inhibition Assays

Procedure

Experiments were performed using purified intracellular domain of c-kit expressed in baculovirus. Estimation of the kinase activity was assessed by the phosphorylation of tyrosine containing target peptide estimated by established ELISA assay.

Experimental Results on Tested Compounds

Result in Table 1 shows the potent inhibitory action of the catalytic activity of c-kit with an IC50<10 µM. Further experiments (not shown) indicates that at least one compound acts as perfect competitive inhibitors of ATP.

TABLE 1

| Compounds | In vitro Inhibition assay results c-kit IC50 (µM) |
|---|---|
| 066; 074; 078; 084; 012; 016; 073; 021; 088; 023; 025; 047; 048; 055; 049; 026; 087; 075; 089; 051; 082; 090; 060; 085; 052; 053; 096 | <10 µM |

Example 2

Ex Vivo TK Inhibition Assays

Procedures

C-Kit WT and Mutated C-Kit (JM) Assay

Proliferation Assays

Cells were washed two times in PBS before plating at $5 \times 10_4$ cells per well of 96-well plates in triplicate and stimulated either with hematopoietic growth factors (HGF) or without. After 2 days of culture, 37 Bq (1.78 Tbq/mmol) of [$_3$H] thymidine (Amersham Life Science, UK) was added for 6 hours. Cells were harvested and filtered through glass fiber filters and [$_3$H] thymidine incorporation was measured in a scintillation counter. For proliferation assay, all drugs were prepared as 20 mM stock solutions in DMSO and conserved at −80° C. Fresh dilutions in PBS were made before each experiment. DMSO dissolved drugs were added at the beginning of the culture. Control cultures were done with corresponding DMSO dilutions. Results are represented in percentage by taking the proliferation without inhibitor as 100%.

Cells

Ba/F3 murine kit and human kit, Ba/F3 mkitΔ27 (juxtamembrane deletion) are derived from the murine IL-3 dependent Ba/F3 proB lymphoid cells. The FMA3 and P815 cell lines are mastocytoma cells expressing endogenous mutated forms of Kit, i.e., frame deletion in the murine juxtamembrane coding region of the receptor-codons 573 to 579. The human leukaemic MC line HMC-1 expresses mutations JM-V560G;

Immunoprecipitation Assays and Western Blotting Analysis

For each assay, $5.10_6$ Ba/F3 cells and Ba/F3-derived cells with various c-kit mutations were lysed and immunoprecipitated as described (Beslu et al., 1996), excepted that cells were stimulated with 250 ng/ml of rmKL. Cell lysates were immunoprecipitated with a rabbit immunserum anti murine KIT, directed against the KIT cytoplasmic domain (Rottapel et al., 1991). Western blot was hybridized either with the 4G10 anti-phosphotyrosine antibody (UBI) or with the rabbit immunserum anti-murine KIT or with different antibodies (described in antibodies paragraph). The membrane was then incubated either with HRP-conjugated goat anti mouse IgG antibody or with HRP-conjugated goat anti rabbit IgG antibody (Immunotech), Proteins of interest were then visualized by incubation with ECL reagent (Amersham).

Experimental Results

The experimental results for various compounds according to the invention using above-described protocols are set forth at Table 2:

TABLE 2

| Target | IC50 (µM) | Compounds |
|---|---|---|
| c-Kit WT | IC50 <10 µM | 002; 005; 006; 007; 008; 009; 010; 012; 017; 019; 020; 021; 023; 024; 025; 026; 028; 029; 030; 032; 042; 043; 045; 047; 048; 049; 050; 051; 052; 053; 054; 055; 056; 057; 059; 060; 061; 062; 063; 064; 065; 066; 067; 072; 073; 074; 075; 077; 078; 079; 080; 081; 082; 083; 084; 085; 086; 087; 088; 089; 090; 092; 093; 094; 095; 096; 097; 106; 105; 104; 103; 128; 129; 130; 131; 117; 110; 116; 124; 108; 122; 111; 113; 118; 107; |
| c-Kit JM Δ27 | IC50 <1 µM | 028; 074; 029; 009; 012; 073; 020; 042; 061; 065; 088; 025; 048; 049; 050; 089; 051; 082; 090; 083; 059; 052; 053; 066; 103; 067; 104; 078; 079; 105; 081; 084; 030; 010; 021; 043; 054; 062; 106; 023; 024; 064; 047; 055; 026; 087; 075; 085; 005; 077; 092; 060; 032; 017; 063; 093; 094; 095; 086; 093; 096; 108; 117; 122; 008; 080; 111; 118; 113; 007; 072; 019; 056; 057; 107; 097; |

Example 3

In Vivo Activity

Procedures

GIST cells: Ba/F3 cells were transfected by c-kit gene having Δ27 mutation (GIST model). Ba/F3 expressing the mutated c-kit gene readily proliferate in the absence of IL3 or SCF and are tumorigenic in nude mice.

Protocol:

Mice were irradiated at J-1 (5Gy)

Tumor cells ($10^6$) were subcutaneously grafted at Jo

Tumor size were daily measured from J14

Number of survival mice were daily estimated

In this experimental model, the tumor size at J14 is about 20 mm$^3$

Treated mice received per os twice a day a dose of 100 mg/kg of one compound of formula II-3 during 5 days (from J26 to J30).

Rhumatoid Arthritis

The mice were pretreated with the compound of formula II-3 (2×, 12.5 mg/kg) for two days (day-2, day-1) before induction of arthritis. Arthritis was induced by ip injection of 150-ul serums at days 0 and 2. The treatment with the compound (2×, 12.5 mg/kg) was continued for 14 days. The control mice were injected with, 1% PBS before the induction of arthritis and during the course of the disease. Ankle thickness and arthritis score was evaluated for 15 days. Arthritis Score: 5 um of scores of each limb (0 no disease; 1 mild swelling of paw or of just a few digits; 2 clear joint inflammation; 3 severe joint inflammation) maximum score=12. Table 3A and Table 3B show the number of mice used in this study. Two sets of experiments were done with different number of mice, one with 4 mices the other with 8 mices.

TABLE 3A

| Treated Mice 2x, 12.5 mg/Kg | C57B1/6 6 |
|---|---|

TABLE 3B

| Controls 2X, 1% PBS | C57B1/6 6 |
|---|---|

Histology

At the end of the experiment the hind limbs were collected. The skin of the limb was removed and the limbs were subsequently fixed in 2% Para formaldehyde.

Experimental Results

GIST

Treated mice (with one compound of formula II-3) displays significant decrease of tumor size at J30 and J33 compared to control.

When administrated per os, one tested compound of the formula II-3 displays a significant antitumor activity against tumors cells expressing c-kit A27.

RA

A compound of the formula II-3 has demonstrated significant activity in the in vivo mouse model of arthritis. Results are shown on FIGS. 1, 2, 3, 4.

Figure 1:
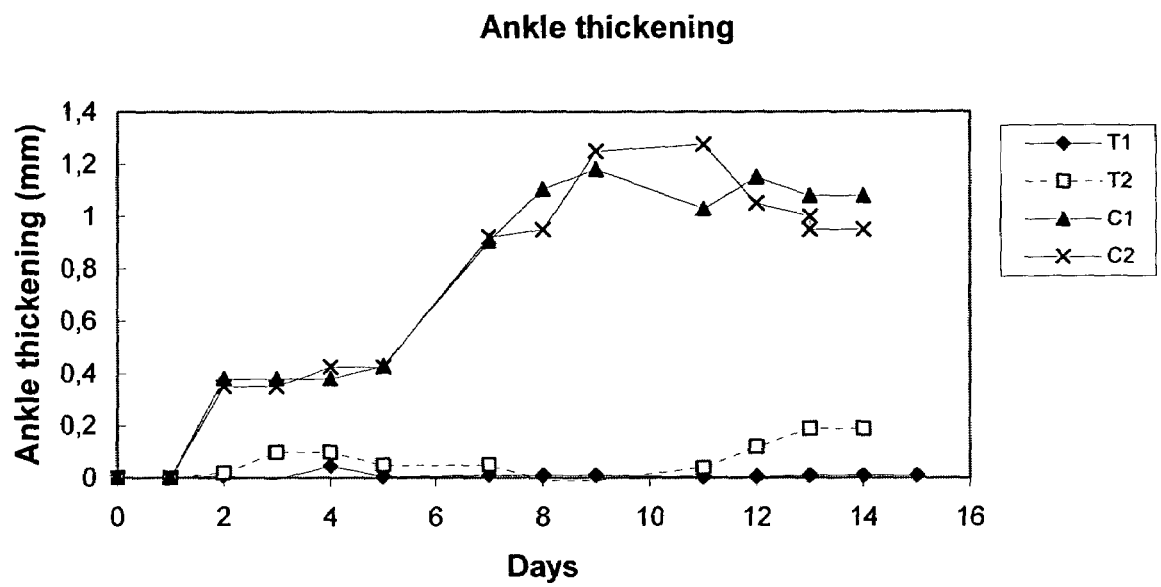
FIG. 1: Effect of the compound in serum transfer experiments, Protocol, ip daily treatment with the compound (2×12.5 mg/kg) and on days-2 and -1, set of experiment with 4 mices (T: treated, C: control)
Figure 2:
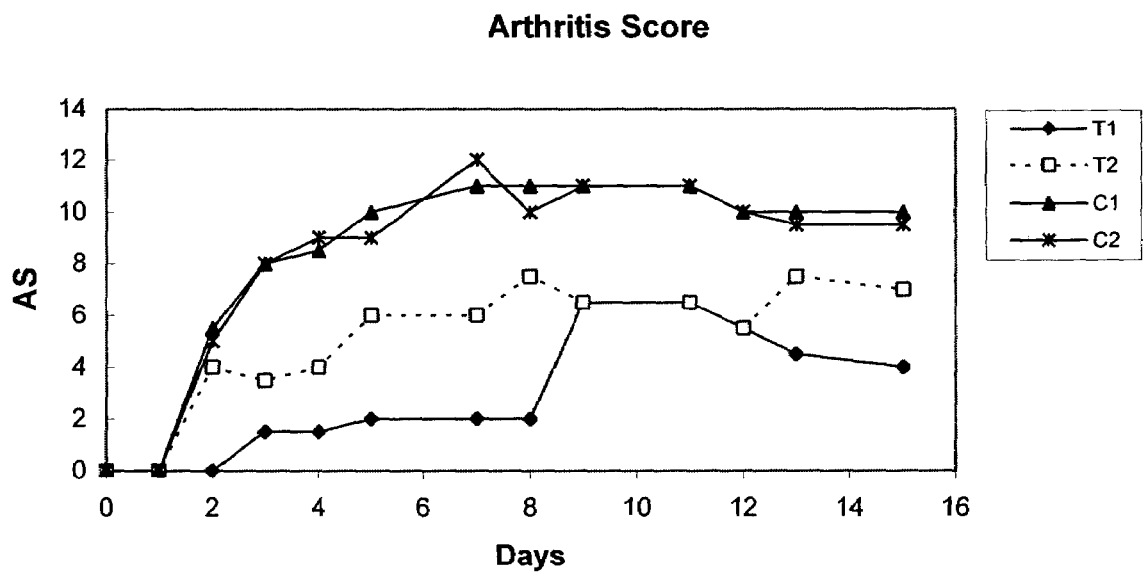
FIG. 2: Effect of the compound in serum transfer experiments, Protocol, ip daily treatment with the compound (2×12.5 mg/kg) and on days-2 and -1, set of experiment with 4 mices (T: treated, C: control)
Figure 3:
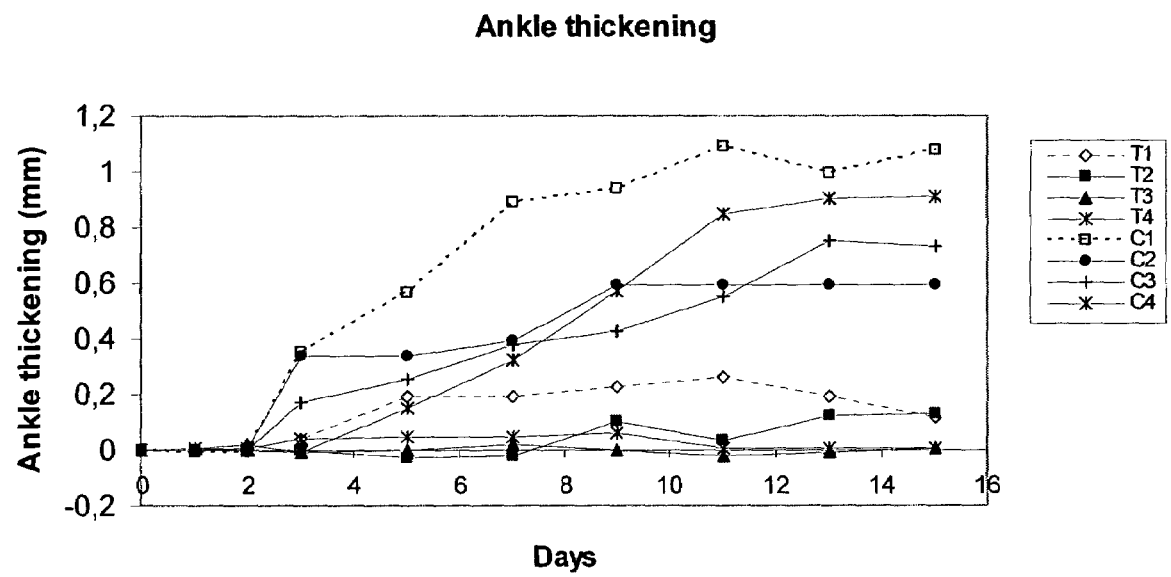
FIG. 3: Effect of the compound in serum transfer experiments, Protocol, ip daily treatment with the compound (2×12.5 mg/kg) and on days -2 and -1, set of experiment with 8 mices (T: treated, C: control)
Figure 4:
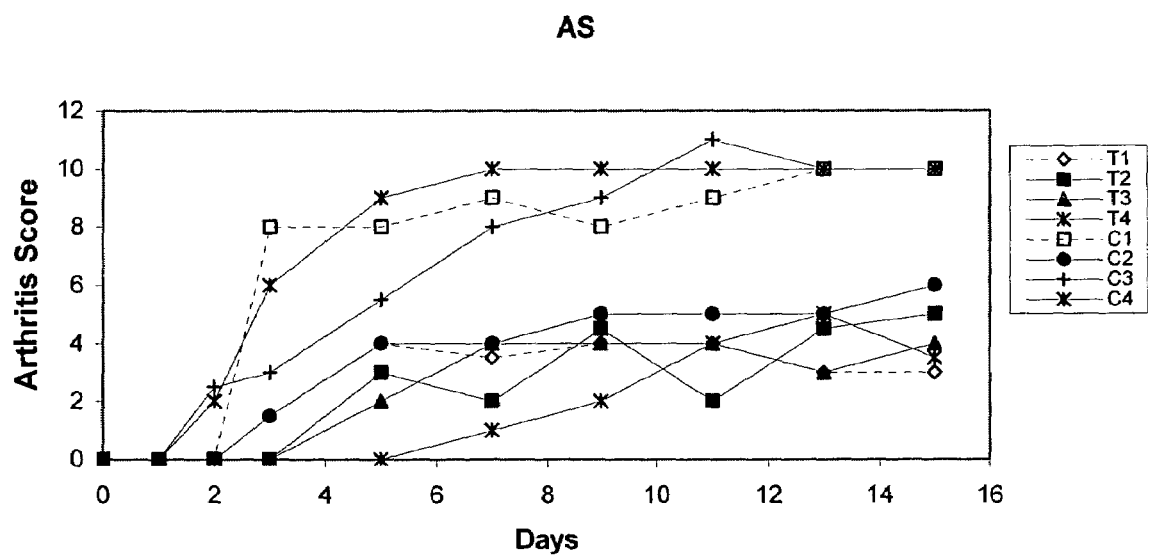
FIG. 4: Effect of the compound in serum transfer experiments, Protocol, ip daily treatment with the compound (2×12.5 mg/kg) and on days-2 and -1, set of experiment with 8 mices (T: treated, C: control)

The invention claimed is:

1. A compound according to the following formula:

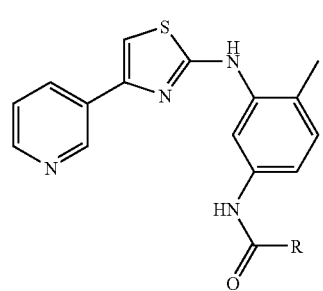

wherein R is:

H or a linear or branched alkyl group containing from 1 to 10 carbon atoms optionally substituted with at least one substituent selected from the group consisting of halogen and a pendant basic nitrogen functionality; or a cycloalkyl, an aryl or heteroaryl group optionally substituted by an alkyl, a cycloalkyl, an aryl or heteroaryl group optionally substituted with at least one substituent selected from the group consisting of a halogen and a pendant basic nitrogen functionality;

wherein said pendent basic nitrogen functionality is selected from the group consisting of

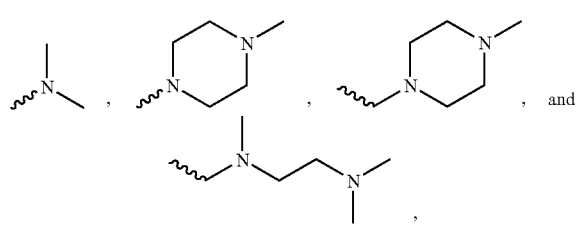

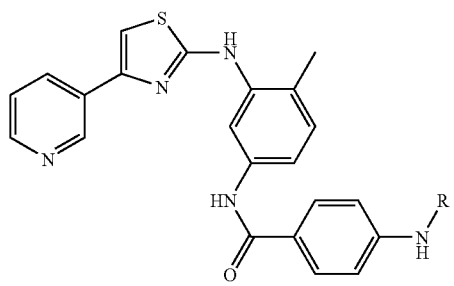

wherein the wavy line corresponds to the point of attachment.

2. A compound according to the following formula:

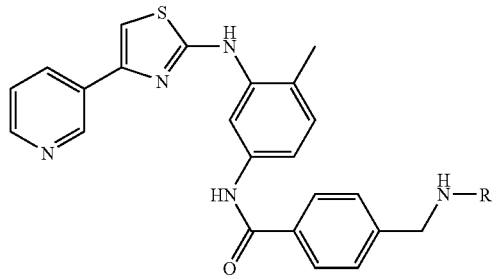

wherein R is:

H or a linear or branched alkyl group containing from 1 to 10 carbon atoms optionally substituted with at least one substituent selected from the group consisting of a halogen and a pendant basic nitrogen functionality, or a cycloalkyl, an aryl or heteroaryl group optionally substituted with at least one substituent selected from I, Cl, Br, F, and a pendant basic nitrogen functionality; or a cycloalkyl, an aryl or heteroaryl group optionally substituted with a cycloalkyl, an aryl or heteroaryl group optionally substituted with at least one substituent selected from I, Cl, Br, F, and a pendant basic nitrogen functionality; or a —SO2-R" group wherein R" is an alkyl, cycloalkyl, aryl or heteroaryl optionally substituted with at least one substituent selected from the group consisting of a halogen and a pendant basic nitrogen functionality; or a —CO—R' or —CO—NR'R" group, wherein R' and R" are independently chosen from H, an alkyl, a cycloalkyl, an aryl or heteroaryl group optionally substituted with at least one substituent selected from the group consisting of a halogen and a pendant basic nitrogen functionality;

wherein said pendent basic nitrogen functionality is selected from the group consistng of

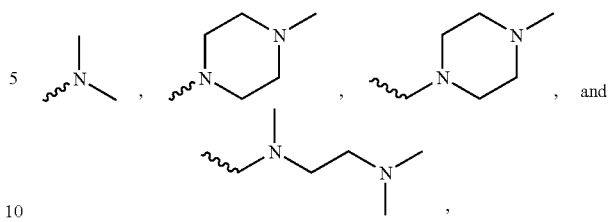

wherein the wavy line corresponds to the point of attachment.

3. A compound according to the following formula:

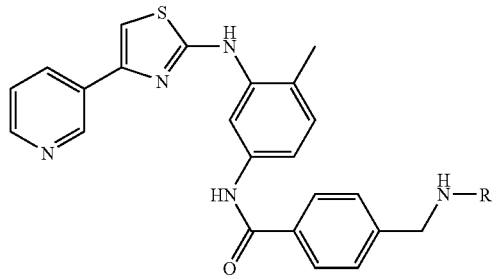

wherein R is H or a linear or branched alkyl group containing from 1 to 10 carbon atoms optionally substituted with at least one substituent selected from the group consisting of a halogen and a pendant basic nitrogen functionality;

a cycloalkyl, aryl or heteroaryl group optionally substituted with at least one substituent selected from the group consisting of a halogen and a pendant basic nitrogen functionality;

an alkyl, cycloalkyl, aryl or heteroaryl group substituted by a alkyl, cycloalkyl, aryl or heteroaryl group optionally substituted with at least one substituent selected from the group consisting of a halogen and a pendant basic nitrogen functionality;

a —SO2-R" group wherein R" is an alkyl, cycloalkyl, aryl or heteroaryl group optionally substituted with at least one substituent selected from the group consisting of a halogen and a pendant basic nitrogen functionality;

a —CO—R' or a —CO—NR'R" group, wherein R' and R" are independently chosen from H or an aryl heteroaryl, alkyl and cycloalkyl group optionally substituted with at least one substituent selected from the group consisting of a halogen and a pendant basic nitrogen functionality;

wherein said pendant basic nitrogen functionality is selected from the group consistng of

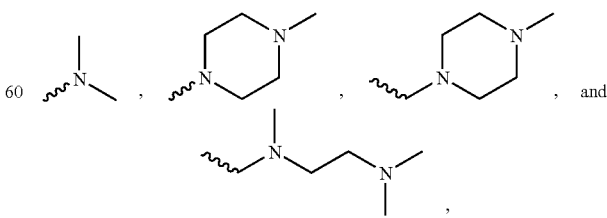

wherein the wavy line corresponds to the point of attachment.

4. A compound according to of the following formula:

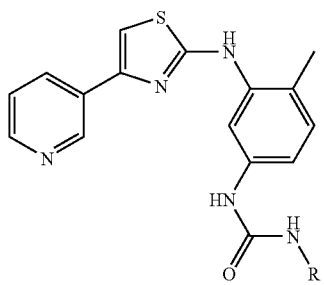

wherein R is:
H or a linear or branched alkyl group containing from 1 to 10 carbon atoms optionally substituted with at least one substituent selected from the group consisting of a halogen and a pendant basic nitrogen functionality; or a cycloalkyl, an aryl or heteroaryl group optionally substituted with at least one substituent selected from the group consisting of a halogen and a pendant basic nitrogen functionality; or a cycloalkyl, an aryl or heteroaryl group substituted by an alkyl, a cycloalkyl, an aryl or heteroaryl group optionally substituted with at least one substituent selected from the group consisting of a halogen and a pendant basic nitrogen functionality;

wherein said pendant basic nitrogen functionality is selected from the group consisting of

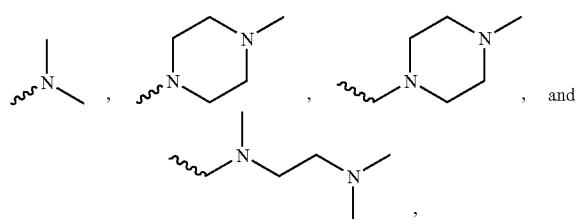

wherein the wavy line corresponds to the point of attachment.

5. A compound according to formula II:

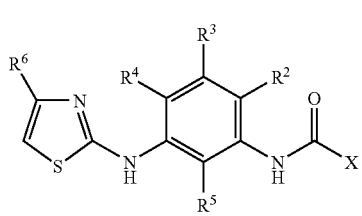

FORMULA II wherein X is R or NRR' and wherein R and R' are independently chosen from H, an aryl, an heteroaryl, an alkyl and a cycloalkyl group optionally substituted with at least one substituent selected from the group consisting of a halogen and a pendant basic nitrogen functionality;

an aryl, an heteroaryl, an alkyl and a cycloalkyl group substituted with an aryl, an heteroaryl, an alkyl and a cycloalkyl group optionally substituted with at least one substituent selected from the group consisting of a halogen and a pendant basic nitrogen functionality;

wherein said pendant basic nitrogen functionality is selected from the group consisting of

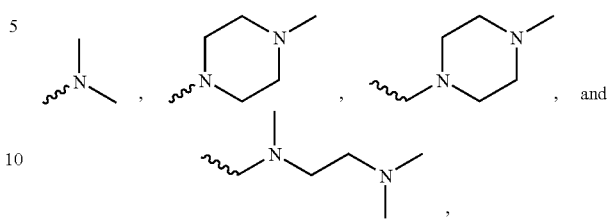

wherein the wavy line corresponds to the point of attachment;

$R^2$ is hydrogen, halogen or a linear or branched alkyl group containing from 1 to 10 carbon atoms, trifluoromethyl or alkoxy;

$R^3$ is hydrogen, halogen or a linear or branched alkyl group containing from 1 to 10 carbon atoms, trifluoromethyl or alkoxy;

$R^4$ is halogen or a linear or branched alkyl group containing from 1 to 10 carbon atoms, trifluoromethyl or alkoxy;

$R^5$ is hydrogen, halogen or a linear or branched alkyl group containing from 1 to 10 carbon atoms, trifluoromethyl or alkoxy;

$R^6$ is one of the following:

(i) an aryl group optionally substituted by one or more substituents such as halogen, alkyl groups containing from 1 to 10 carbon atoms, trifluoromethyl, or alkoxy;

(ii) a heteroaryl group such as a 2, 3, or 4-pyridyl group, which may additionally bear one or more substituents;

(iii) a five-membered ring aromatic heterocyclic group such as for example 2-thienyl, 3-thienyl, 2-thiazolyl, 4-thiazolyl, or 5-thiazolyl, which may additionally bear one or more substituents.

6. A compound according to claim 5 selected from the group consisting of:

1-(4-Bromo-phenyl)-3-[4-methyl-3-(4-pyridin-3-yl-thiazol-2-ylamino)-phenyl]-urea (example 010);

1-(4-Fluoro-phenyl)-3-[4-methyl-3-(4-pyridin-3-yl-thiazol-2-ylamino)-phenyl]-urea (example 012);

1-[4-Methyl-3-(4-pyridin-3-yl-thiazol-2-ylamino)-phenyl]-3-thiophen-2-yl-urea (example 015);

1-(3,5-Dimethyl-isoxazol-4-yl)-3-[4-methyl-3-(4-pyridin-3-yl-thiazol-2-ylamino)-phenyl]-urea (example 019);

1-(2-Iodo-phenyl)-3-[4-methyl-3-(4-pyridin-3-yl-thiazol-2-ylamino)-phenyl]-urea (example 020); and 1-(4-Dimethylamino-phenyl)-3-[4-methyl-3-(4-pyridin-3-yl-thiazol-2-ylamino)-phenyl]-urea (example 022).

7. A compound according to claim 5, wherein X is selected from the structures (a)-(d) and (f) shown below:

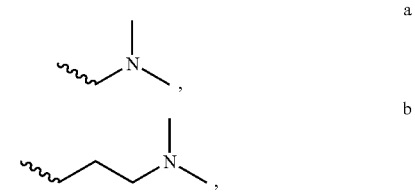

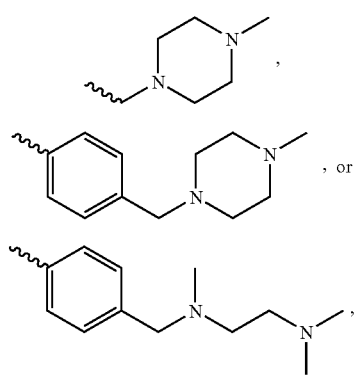

wherein the wavy line corresponds to the point of attachment to core structure of formula II.

8. A compound according to claim 7, wherein X is group (d) and R⁶ is a 3-pyridyl group.

9. A compound according to claim 7, wherein X is group (d) and R⁴ is a methyl group.

10. A compound according to claim 7, wherein X is group (d) and R² and/or R³ and/or R⁵ is H.

11. The compound of claim 5 which is: 4-(4-methyl-piperazin-1-ylmethyl)-N-[4-methyl-3-(4-pyridin-4-yl-thiazol-2-ylamino)-phenyl]-benzamide (example 080).

12. A compound which is: N-{3-[4-(4-cyano-phenyl)-thiazol-2-ylamino]}-4-methyl-phenyl)-4-(4-methyl-piperazin-1-ylmethyl)-benzamide (example 081).

13. The compound of claim 5 which is: 4-(4-methyl-piperazin-1-yl)-N-[4-methyl-3-(4-pyridin-3-yl-thiazol-2-ylamino)-phenyl]-benzamide (example 060) or 4-(4-methyl-piperazin-1-ylmethyl)-N-[4-methyl-3-(4-pyridin-3-yl-thiazol-2-ylamino)-phenyl]-benzamide (example 066).

14. A compound which is: 4-(4-methyl-piperazin-1-ylmethyl)-N-[4-methyl-3-(4-pyridin-3-yl-thiazol-2-ylamino)-phenyl]-benzamide (example 066).

15. A composition comprising a compound of claim 14 and a pharmaceutically acceptable carrier.

16. A compound of formula I:

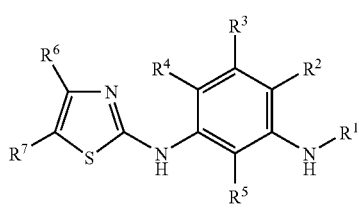

FORMULA I wherein R¹ is:
—C(O)R, —C(O)OR, or —CO—NRR', wherein R and R' are independently selected from the group consisting of hydrogen, aryl, heteroaryl, alkyl, and cycloalkyl, each optionally substituted with at least one substituent selected from the group consisting of halogen and a pendant basic nitrogen functionality;

R² is hydrogen, halogen or a linear or branched alkyl group containing from 1 to 10 carbon atoms, trifluoromethyl or alkoxy;

R³ is hydrogen, halogen or a linear or branched alkyl group containing from 1 to 10 carbon atoms, trifluoromethyl or alkoxy;

R⁴ is halogen or a linear or branched alkyl group containing from 1 to 10 carbon atoms, trifluoromethyl or alkoxy;

R⁵ is hydrogen, halogen or a linear or branched alkyl group containing from 1 to 10 carbon atoms, trifluoromethyl or alkoxy;

R⁶ is one of the following:
(i) an aryl group such as phenyl optionally substituted by one or more substituents such as halogen, alkyl groups containing from 1 to 10 carbon atoms, trifluoromethyl, or alkoxy;
(ii) a heteroaryl group such as a 2, 3, or 4-pyridyl group, which may additionally bear one or more substituents; or
(iii) a five-membered ring aromatic heterocyclic group such as for example 2-thienyl, 3-thienyl, 2-thiazolyl, 4-thiazolyl, or 5-thiazolyl, which may additionally bear one or more substituents;

and R⁷ is one of the following:
(i) an aryl group such as phenyl optionally substituted by one or more substituents;
(ii) a heteroaryl group such as a 2, 3, or 4-pyridyl group, which may additionally bear one or more substituents;
(iii) a five-membered ring aromatic heterocyclic group such as for example 2-thienyl, 3-thienyl, 2-thiazolyl, 4-thiazolyl, or 5-thiazolyl, which may additionally bear one or more substituents; or
(iv) H, a halogen selected from I, F, Cl or Br; NH₂, NO₂ and SO₂—R", wherein R" is a linear or branched alkyl group optionally substituted with at least one substituent selected from the group consisting of halogen and a pendant basic nitrogen functionality;
wherein said pendant basic nitrogen functionality is selected from the group consisting of

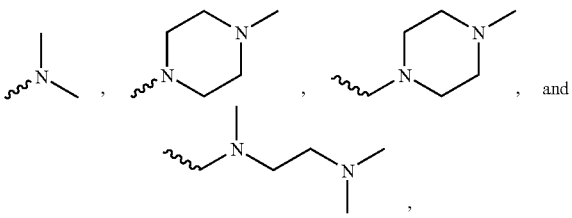

, and wherein the wavy line corresponds to the point of attachment.

17. A composition comprising a compound of claim 16 in a pharmaceutically acceptable carrier.

18. A compound according to claim 16, wherein R' is
—C(O)R, wherein R is independently selected from the group consisting of hydrogen, aryl, heteroaryl, alkyl, and cycloalkyl, each optionally substituted with at least one substituent selected from the group consisting of halogen and a pendant basic nitrogen functionality;
wherein said pendant basic nitrogen functionality is selected from selected from the group consisting of

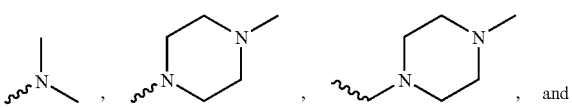

, and

-continued

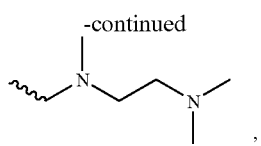

wherein the wavy line corresponds to the point of attachment.

19. A compound according to claim 18 selected from the group consisting of:
- N-[4-Methyl-3-(4-phenyl-thiazol-2-ylamino)-phenyl]-4-(4-methyl-piperazin-1-ylmethyl)-benzamide (example 004);
- N-[3-([2,4']Bithiazolyl-2'-ylamino)-4-methyl-phenyl]-4-(4-methyl-piperazin-1-ylmethyl)-benzamide; (example 005);
- N-[4-Chloro-3-(4-pyridin-3-yl-thiazol-2-ylamino)-phenyl]-4-(4-methyl-piperazin-1-ylmethyl)-benzamide (example 027);
- 3-Bromo-N-[4-methyl-3-(4-pyridin-3-yl-thiazol-2-ylamino)-phenyl]-benzamide (example 028);
- 3-Iodo-N-[4-methyl-3-(4-pyridin-3-yl-thiazol-2-ylamino)-phenyl]-benzamide (example 029);
- 2-Iodo-N-[4-methyl-3-(4-pyridin-3-yl-thiazol-2-ylamino)-phenyl]-benzamide (example 032);
- 4-Iodo-N-[4-methyl-3-(4-pyridin-3-yl-thiazol-2-ylamino)-phenyl]-benzamide (example 033);
- 3-Fluoro-N-[4-methyl-3-(4-pyridin-3-yl-thiazol-2-ylamino)-phenyl]-benzamide (example 045);
- 4-Dimethylamino-N-[4-methyl-3-(4-pyridin-3-yl-thiazol-2-ylamino)-phenyl]-benzamide (example 047);
- 4-(4-Methyl-piperazin-1-yl)-N-[4-methyl-3-(4-pyridin-3-yl-thiazol-2-ylmethyl)-phenyl]-benzamide (example 060);
- N-[4-Methyl-3-(4-pyridin-3-yl-thiazol-2-ylamino)-phenyl]-isonicotinamide (example 063);
- 2,6-Dichloro-N-[4-methyl-3-(4-pyridin-3-yl-thiazol-2-ylamino)-phenyl]-isonicotinamide (example 064);
- 3,5-Dibromo-4-(4-methyl-piperazin-1-ylmethyl)-N-[4-methyl-3-(4-pyridin-3-yl-thiazol-2-ylamino)-phenyl]-benzamide (example 067);
- 3-Fluoro-4-(4-methyl-piperazin-1-ylmethyl)-N-[4-methyl-3-(4-pyridin-3-yl-thiazol-2-ylamino)-phenyl]-benzamide (example 074);
- 2,3,5,6-Tetrafluoro-4-(4-methyl-piperazin-1-ylmethyl)-N-[4-methyl-3-(4-pyridin-3-yl-thiazol-2-ylamino)-phenyl]-benzamide (example 076);
- N-{3-[4-(4-Fluoro-phenyl)-thiazol-2-ylamino]-4-methyl-phenyl}-4-(4-methyl-piperazin-1-ylmethyl)-benzamide (example 077);
- 3-Bromo-4-(4-methyl-piperazin-1-ylmethyl)-N-[4-methyl-3-(4-pyridin-3-yl-thiazol-2-ylamino)-phenyl]-benzamide (example 078);
- 3-Chloro-4-(4-methyl-piperazin-1-ylmethyl)-N-[4-methyl-3-(4-pyridin-3-yl-thiazol-2-ylamino)-phenyl]-benzamide (example 079);
- N-{4-Methyl-3-[4-(5-methyl-pyridin-3-yl)-thiazol-2-ylamino]-phenyl}-4-(4-methyl-piperazin-1-ylmethyl)-benzamide (example 084);
- 3-Iodo-4-(4-methyl-piperazin-1-ylmethyl)-N-[4-methyl-3-(4-pyridin-3-yl-thiazol-2-ylamino)-phenyl]-benzamide (example 085);
- 3-Dimethylamino-N-[4-methyl-3-(4-pyridin-3-yl-thiazol-2-ylamino)-phenyl]-benzamide (example 088);
- 3-(4-Methyl-piperazin-1-yl)-N-[4-methyl-3-(4-pyridin-3-yl-thiazol-2-ylamino)-phenyl]-benzamide (example 089);
- Cyclohexanecarboxylic acid [4-methyl-3-(4-pyridin-3-yl-thiazol-2-ylamino)-phenyl]-amide (example 092);
- 5-[4-Methyl-3-(4-pyridin-3-yl-thiazol-2-ylamino)-phenylcarbamoyl]-pentanoic acid ethyl ester (example 093);
- 4-Fluoro-N-[4-methyl-3-(4-pyridin-3-yl-thiazol-2-ylamino)-phenyl]-benzamide (example 104);
- N-{3-[4-(4-Chloro-phenyl)-thiazol-2-ylamino]-4-methyl-phenyl}-4-(4-methyl-piperazin-1-ylmethyl)-benzamide (example 108);
- N-{3-[4-(4-Methoxy-phenyl)-thiazol-2-ylamino]-4-methyl-phenyl}-4-(4-methyl-piperazin-1-ylmethyl)-benzamide (example 110);
- N-{3-[4-(3-Fluoro-phenyl)-thiazol-2-ylamino]-4-methyl-phenyl}-4-(4-methyl-piperazin-1-ylmethyl)-benzamide (example 111);
- N-{3-[4-(3-Methoxy-phenyl)-thiazol-2-ylamino]-4-methyl-phenyl}-4-(4-methyl-piperazin-1-ylmethyl)-benzamide(example 113);
- 4-(4-Methyl-piperazin-1-ylmethyl)-N-{4-methyl-3-[4-(3-trifluoromethyl-phenyl)-thiazol-2-ylamino]-phenyl}-benzainide (example 116);
- N-{3-[4-(2-Fluoro-phenyl)-thiazol-2-ylamino]-4-methyl-phenyl}-4-(4-methyl-piperazin-1-ylmethyl)-benzainide (example 118);
- 4-(4-Methyl-piperazin-1-ylmethyl)-N-[4-methyl-3-(4-pyridin-2-y-1-thiazol-2-ylamino)-phenyl]-benzamide (example 122); and
- N-{3-[4-(2,5-Dimethyl-phenyl)-thiazol-2-ylamino]-4-methyl-phenyl}-4-(4-methyl-piperazin-1-ylmethyl)-benzainide (example 124).

20. A pharmaceutical composition comprising a compound according to claim 18 and a pharmaceutically acceptable carrier.

21. A compound according to claim 16, wherein R' is —CO—NRR', wherein R and R' are independently selected from the group consisting of hydrogen, aryl, heteroaryl, alkyl, and cycloalkyl, each optionally substituted with at least one substituent selected form the group consisting of halogen and a pendant basic rntrogen functionality;
wherein said pendant basic nitrogen functionality is selected from the group consisting of

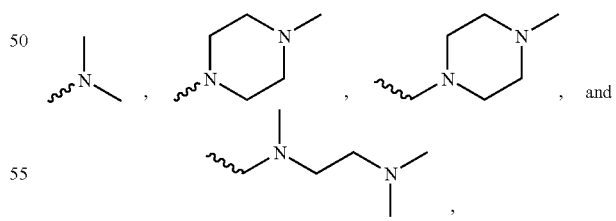

wherein the wavy line corresponds to the point of attachment.

22. A compound according to claim 21 selected from the group consisting of:
- 1-(2-Fluoro-phenyl)-3-[4-methyl-3-(4-pyridin-3-yl-thiazol-2-ylamino)-phenyl]-urea (example 023);
- 1-(2-Chloro-phenyl)-3-[4-methyl-3-(4-pyridin-3-yl-thiazol-2-ylamino)-phenyl]-urea (example 024); and
- 1-(3-Fluoro-phenyl)-3-[4-methyl-3-(4-pyridin-3-yl-thiazol-2-ylamino)-phenyl]-urea (example 025).

23. A pharmaceutical composition comprising a compound according to claim 21 and a pharmaceutically acceptable carrier.

24. A compound according to claim 16, wherein R' is —C(O)OR, wherein R is selected from the group consisting of hydrogen, aryl, heteroaryl, alkyl, and cycloalkyl, each optionally substituted with at least one substituent selected form the group consisting of halogen and a pendant basic nitrogen functionality;
wherein said pendant basic nitrogen functionality is selected from the group consistinig of

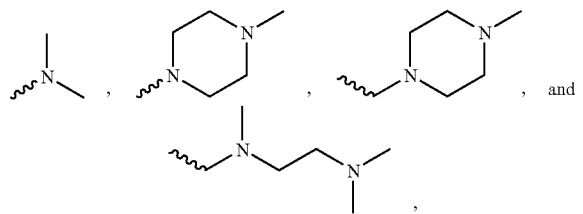

wherein the wavy line corresponds to the point of attachment.

25. A compound according to claim 24 selected from the group consisting of:
[4-Methyl-3-(4-pyridin-3-yl-thiazol-2-ylamino)-phenyl]-carbamic acid isobutyl ester (example 097), and
[4-Methyl-3-(4-pyridin-3-yl-thiazol-2-ylamino)-phenyl]-carbamic acid tert-butyl ester (example 098).

26. A pharmaceutical composition comprising a compound according to claim 25 and a pharmaceutically acceptable carrier.

27. A compound according to the following formula:

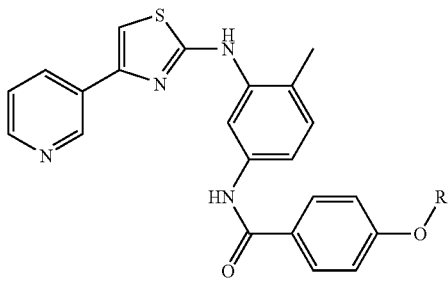

wherein R is H or a linear or branched alkyl group containing from 1 to 10 carbon atoms optionally substituted with at least one heteroatom, or bearing at least one pendant basic nitrogen functionality;
a cycloalkyl, aryl or heteroaryl group optionally substituted with at least one substituent selected from the group consisting of a halogen and a pendant basic nitrogen functionality; or
an alkyl, cycloalkyl, aryl or heteroaryl group substituted by a alkyl, cycloalkyl, aryl or heteroaryl group optionally substituted with at least one substituent selected from the group consisting of a halogen and a pendant basic nitrogen functionality; or
a —SO2-R" group wherein R" is an alkyl, cycloalkyl, aryl or heteroaryl group optionally substituted with at least one substituent selected from the group consisting of a halogen and a pendant basic nitrogen functionality;
a —CO—R' or a —CO—NR'R"—group wherein R' and R" are independently chosen from H or an aryl heteroaryl, alkyl and cycloalkyl group optionally substituted with at least one substituent selected from the group consistiiw of a halogen and a pendant basic nitrogen functionality;
wherein said pendant basic nitrogen functionality is selected from the group consisting of selected from the group consisting of

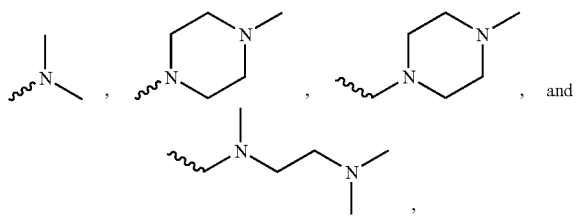

wherein the wavy line corresponds to the point of attachment.

28. A compound according to claim 27 selected from the group consisting of
4-Hydroxy-N-[4-methyl-3-(4-pyridin-3-yl-thiazol-2-ylamino)-phenyl]-benzamide(example 037);
Thiophene-2-sulfonic acid 4-[4-methyl-3-(4-pyridin-3-yl-thiazol-2-ylamino)-phenylcarbamoyl]-phenyl ester (example 042);
4-Iodo-benzenesulfonic acid 4-[4-methyl-3-(4-pyridin-3-yl-thiazol-2-ylamino)-phenylcarbamoyl]-phenyl ester (example 043);
4-Isopropoxy-N-[4-methyl-3-(4-pyridin-3-yl-thiazol-2-ylamino)-phenyl]-benzamide (example 050);
N-[4-Methyl-3-(4-pyridin-3-yl-thiazol-2-ylamino)-phenyl]-3-(2-morpholin-4-yl-ethoxy)-benzamide (example 052);
3-Fluoro-benzenesulfonic acid 4-[4-methyl-3-(4-pyridin-3-yl-thiazol-2-ylamino)-phenylcarbamoyl]-phenyl ester (example 056);
2-Fluoro-benzenesulfonic acid 4-[4-methyl-3-(4-pyridin-3-yl-thiazol-2-ylamino)-phenylcarbamoyl]-phenyl ester (example 058); and
3-Methoxy-N-[4-methyl-3-(4-pyridin-3-yl-thiazol-2-ylamino)-phenyl]-benzamide (example 059).

29. A compound according to claim 2 selected from the group consisting of
4-[3-(4-Bromo-phenyl)-ureido]-N-[4-methyl-3-(4-pyridin-3-yl-thiazol-2-ylamino)-phenyl]-benzamide(example 036);
N-[4-Methyl-3-(4-pyridin-3-yl-thiazol-2-ylamino)-phenyl]-4-(3-thiophen-2-yl-ureido)-benzamide (example 038);
N-[4-Methyl-3-(4-pyridin-3-yl-thiazol-2-ylamino)-phenyl]-4-(thiophene-2-sulfonylamino)-benzamide (example 044);
4-[3-(2-Iodo-phenyl)-ureido]-N-[4-methyl-3-(4-pyridin-3-yl-thiazol-2-ylamino)-phenyl]-benzamide (example 101); and
4-[3-(4-Fluoro-phenyl)-ureido]-N-[4-methyl-3-(4-pyridin-3-yl-thiazol-2-ylamino)-phenyl]-benzamide (example 102).

30. A compound selected from the group consisting of
1-(4-Methoxy-phenyl)-3-[4-methyl-3-(4-pyridin-3-yl-thiazol-2-ylamino)-phenyl]-urea (example 009);
1-[4-Methyl-3-(4-pyridin-3-yl-thiazol-2-ylamino)-phenyl]-3-(4-trifluoromethyl-phenyl)-urea (example 011);
1-[4-Methyl-3-(4-pyridin-3-yl-thiazol-2-ylamino)-phenyl]-3-(3,4,5-trimethoxy-phenyl)-urea (example 013);

4-{3-[4-Methyl-3-(4-pyridin-3-yl-thiazol-2-ylamino)-phenyl]-ureido}-benzoic acid ethyl ester (example 014);

1-Cyclohexyl-1-(N-Cyclohexyl-formamide)-3-[4-methyl-3-(4-pyridin-3-yl-thiazol-2-ylamino)-phenyl]-urea (example 016);

1-(2,4-Dimethoxy-phenyl)-3-[4-methyl-3-(4-pyridin-3-yl-thiazol-2-ylamino)-phenyl]-urea (example 017);

1-(2-Iodo-phenyl)-1-(N-(2-Iodo-phenyl)-formamide)-3-[4-methyl-3-(4-pyridin-3-yl-thiazol-2-ylamino)-phenyl]-urea (example 018);

1-(4-Difluoromethoxy-phenyl)-3-[4-methyl-3-(4-pyridin-3-yl-thiazol-2-ylamino)-phenyl]-urea (example 021);

1-[4-Methyl-3-(4-pyridin-3-yl-thiazol-2-ylamino)-phenyl]-3-p-tolyl-urea (example 026);

(4-Hydroxymethyl-N-[4-methyl-3-(4-pyridin-3-yl-thiazol-2-ylamino)-phenyl]-benzamide (example 030);

4-(3-{4-[4-Methyl-3-(4-pyridin-3-yl-thiazol-2-ylamino)-phenylcarbamoyl]-phenyl}-ureido)-benzoic acid ethyl ester (example 034);

N-[4-Methyl-3-(4-pyridin-3-yl-thiazol-2-ylamino)-phenyl]-4-[3-(4-trifluoromethyl-phenyl)-ureido]-benzamide (example 035);

4-[3-(3,5-Dimethyl-isoxazol-4-yl)-ureido]-N-[4-methyl-3-(4-pyridin-3-yl-thiazol-2-ylamino)-phenyl]-benzamide (example 039);

4-[3-(4-Methoxy-phenyl)-ureido]-N-[4-methyl-3-(4-pyridin-3-yl-thiazol-2-ylamino)-phenyl]-benzamide (example 040);

4-[3-(4-Difluoromethoxy-phenyl)-ureido]-N-[4-methyl-3-(4-pyridin-3-yl-thiazol-2-ylamino)-phenyl]-benzamide (example 041);

2-Fluoro-5-methyl-N-[4-methyl-3-(4-pyridin-3-yl-thiazol-2-ylamino)-phenyl]-benzamide (example 048);

4-tert-Butyl-N-[4-methyl-3-(4-pyridin-3-yl-thiazol-2-ylamino)-phenyl]-benzamide (example 049);

Benzo[1,3]dioxole-5-carboxylic acid [4-methyl-3-(4-pyridin-3-yl-thiazol-2-ylamino)-phenyl]-amide (example 051);

3-Cyano-N-[4-methyl-3-(4-pyridin-3-yl-thiazol-2-ylamino)-phenyl]-benzamide (example 054);

2-Fluoro-N-[4-methyl-3-(4-pyridin-3-yl-thiazol-2-ylamino)-phenyl]-3-trifluoromethyl-benzamide (example 055);

3-Methyl-N-[4-methyl-3-(4-pyridin-3-yl-thiazol-2-ylamino)-phenyl]-benzamide (example 061);

Biphenyl-3-carboxylic acid [4-methyl-3-(4-pyridin-3-yl-thiazol-2-ylamino)-phenyl]-amide (example 062);

N-[4-Methyl-3-(4-pyridin-3-yl-thiazol-2-ylamino)-phenyl]-3-trifluoromethyl-benzamide (example 065);

{4-[4-Methyl-3-(4-pyridin-3-yl-thiazol-2-ylamino)-phenylcarbamoyl]-benzyl}-carbamic acid tert-butyl ester (example 073);

3-Fluoro-4-(4-methyl-piperazin-1-ylmethyl)-N-[4-methyl-3-(4-pyridin-3-yl-thiazol-2-ylamino)-phenyl]-benzamide (example 074);

4-(4-Methyl-piperazin-1-ylmethyl)-N-[4-methyl-3-(4-pyridin-3-yl-thiazol-2-ylamino)-phenyl]-3-trifluoromethyl-benzamide (example 075);

4-(1-Methoxy-ethyl)-N-[4-methyl-3-(4-pyridin-3-yl-thiazol-2-ylamino)-phenyl]-benzamide (example 083);

N-[4-Methyl-3-(4-pyridin-3-yl-thiazol-2-ylamino)-phenyl]-4-[3-(4-trifluoromethyl-phenyl)-ureidomethyl]-benzamide (example 086);

4-Cyano-N-[4-methyl-3-(4-pyridin-3-yl-thiazol-2-ylamino)-phenyl]-benzamide (example 103);

4-[3-(2,4-Dimethoxy-phenyl)-ureido]-N-[4-methyl-3-(4-pyridin-3-yl-thiazol-2-ylamino)-phenyl]-benzamide (example 100); and 3-Bromo-4-methyl-N-[4-methyl-3-(4-pyridin-3-yl-thiazol-2-ylamino)-phenyl]-benzamide (example 105).

\* \* \* \* \*